US011488721B2

United States Patent
Otto et al.

(10) Patent No.: US 11,488,721 B2
(45) Date of Patent: *Nov. 1, 2022

(54) OPERATIVELY TUNING IMPLANTS FOR INCREASED PERFORMANCE

(71) Applicant: Smith & Nephew, Inc., Memphis, TN (US)

(72) Inventors: Jason K. Otto, Plantation, FL (US); Brian W. McKinnon, Arlington, TN (US); Mark Ellsworth Nadzadi, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 404 days.

This patent is subject to a terminal disclaimer.

(21) Appl. No.: 16/825,943

(22) Filed: Mar. 20, 2020

(65) Prior Publication Data
US 2020/0219626 A1    Jul. 9, 2020

Related U.S. Application Data

(63) Continuation of application No. 15/088,697, filed on Apr. 1, 2016, now Pat. No. 10,600,515, which is a
(Continued)

(51) Int. Cl.
*G16H 50/50* (2018.01)
*B33Y 50/00* (2015.01)
(Continued)

(52) U.S. Cl.
CPC .............. *G16H 50/50* (2018.01); *A61B 5/103* (2013.01); *A61B 5/4528* (2013.01);
(Continued)

(58) Field of Classification Search
CPC ........ G16H 50/50; G16H 20/40; A61B 5/103; A61B 5/4528; A61B 34/10; B33Y 50/00; B33Y 80/00; G16B 5/00; A61F 2/38
See application file for complete search history.

(56) References Cited

U.S. PATENT DOCUMENTS

| 4,436,684 A | 3/1984 | White |
| 4,646,729 A | 3/1987 | Kenna et al. |

(Continued)

FOREIGN PATENT DOCUMENTS

| DE | 3522196 A1 | 2/1986 |
| DE | 3626549 A1 | 2/1988 |
| DE | 4304572 A1 | 8/1994 |
| EP | 0908836 A2 | 4/1999 |

(Continued)

OTHER PUBLICATIONS

"Implant", Merriam-Webster Online Dictionary, www.m-w.com (Original access date Jan. 11, 2007).
(Continued)

*Primary Examiner* — Bijan Mapar
(74) *Attorney, Agent, or Firm* — KDB Firm PLLC

(57) ABSTRACT

A method for preoperatively characterizing an individual patient's biomechanic function in preparation of implanting a prosthesis is provided. The method includes subjecting a patient to various activities, recording relative positions of anatomy during said various activities, measuring force environments responsive to said patient's anatomy and affected area during said various activities, characterizing the patient's biomechanic function from said relative positions and corresponding force environments, inputting the measured force environments, relative positions of knee anatomy, and patient's biomechanic function characterization into one or more computer simulation models, inputting a computer model of the prosthesis into said one or more computer simulation models, and manipulating the placement of the prosthesis in the computer simulation using said patient's biomechanic function characterization and said computer model of the prosthesis to approximate a preferred biomechanical fit of the prosthesis.

18 Claims, 13 Drawing Sheets

Related U.S. Application Data continuation of application No. 13/951,009, filed on Jul. 25, 2013, now abandoned, which is a continuation of application No. 13/302,256, filed on Nov. 22, 2011, now Pat. No. 8,521,492, which is a continuation of application No. 12/234,444, filed on Aug. 19, 2008, now Pat. No. 8,078,440.

(51) Int. Cl.
| | | |
|---|---|---|
| *A61B 5/103* | (2006.01) | |
| *A61B 5/00* | (2006.01) | |
| *G16H 20/40* | (2018.01) | |
| *G16H 20/30* | (2018.01) | |
| *A61B 34/10* | (2016.01) | |
| *A61F 2/38* | (2006.01) | |
| *A61F 2/30* | (2006.01) | |
| *B33Y 80/00* | (2015.01) | |
| *G16B 5/00* | (2019.01) | |
| *G16H 30/20* | (2018.01) | |

(52) U.S. Cl.
CPC ............ *A61B 5/4824* (2013.01); *A61B 34/10* (2016.02); *B33Y 50/00* (2014.12); *B33Y 80/00* (2014.12); *G16B 5/00* (2019.02); *G16H 20/30* (2018.01); *G16H 20/40* (2018.01); *G16H 30/20* (2018.01); *A61B 5/4533* (2013.01); *A61B 5/6878* (2013.01); *A61B 2034/108* (2016.02); *A61F 2/38* (2013.01); *A61F 2002/3096* (2013.01); *A61F 2002/30943* (2013.01); *A61F 2002/30955* (2013.01)

(56) References Cited

U.S. PATENT DOCUMENTS

| | | |
|---|---|---|
| 4,703,751 A | 11/1987 | Pohl |
| 4,704,686 A | 11/1987 | Aldinger |
| 4,759,350 A | 7/1988 | Dunn et al. |
| 4,822,365 A | 4/1989 | Walker et al. |
| 4,841,975 A | 6/1989 | Woolson |
| 4,936,862 A | 6/1990 | Walker et al. |
| 4,940,412 A | 7/1990 | Blumenthal |
| 5,042,504 A | 8/1991 | Huberti |
| 5,098,383 A | 3/1992 | Hemmy et al. |
| 5,129,908 A | 7/1992 | Petersen |
| 5,274,565 A | 12/1993 | Reuben |
| 5,365,996 A | 11/1994 | Crook |
| 5,370,692 A | 12/1994 | Fink et al. |
| 5,417,694 A | 5/1995 | Marik et al. |
| 5,533,519 A | 7/1996 | Radke et al. |
| 5,554,190 A | 9/1996 | Draenert |
| 5,595,703 A | 1/1997 | Swaelens et al. |
| 5,609,640 A | 3/1997 | Johnson |
| 5,682,886 A | 11/1997 | Delp et al. |
| 5,735,277 A | 4/1998 | Schuster |
| 5,741,215 A | 4/1998 | D'Urso |
| 5,761,125 A | 6/1998 | Mastrorio |
| 5,768,134 A | 6/1998 | Swaelens et al. |
| 5,824,085 A | 10/1998 | Sahay et al. |
| 5,860,981 A | 1/1999 | Berlin et al. |
| 5,871,018 A | 2/1999 | Delp et al. |
| 5,871,546 A | 2/1999 | Colleran et al. |
| 5,880,976 A | 3/1999 | DiGioia III et al. |
| 5,885,296 A | 3/1999 | Masini |
| 5,925,049 A | 7/1999 | Gustilo et al. |
| 5,935,171 A | 8/1999 | Schneider et al. |
| 5,961,456 A | 10/1999 | Gildenberg |
| 5,995,738 A | 11/1999 | DiGioia, III et al. |
| 6,002,859 A | 12/1999 | DiGioia, III et al. |
| 6,033,415 A | 3/2000 | Mittelstadt et al. |
| 6,126,690 A | 10/2000 | Ateshian et al. |
| 6,170,488 B1 | 1/2001 | Spillman, Jr. et al. |
| 6,171,252 B1 | 1/2001 | Roberts |
| 6,205,411 B1 | 3/2001 | DiGioia, III et al. |
| 6,206,835 B1 | 3/2001 | Spillman, Jr. et al. |
| 6,206,927 B1 | 3/2001 | Fell et al. |
| 6,322,567 B1 | 11/2001 | Mittelstadt et al. |
| 6,447,448 B1 | 9/2002 | Ishikawa et al. |
| 6,510,334 B1 | 1/2003 | Schuster et al. |
| 6,520,964 B2 | 2/2003 | Tallarida et al. |
| 6,540,786 B2 | 4/2003 | Chibrac et al. |
| 6,560,476 B1 | 5/2003 | Pelletier et al. |
| 6,583,630 B2 | 6/2003 | Mendes et al. |
| 6,610,096 B2 | 8/2003 | MacDonald |
| 6,621,278 B2 | 9/2003 | Ariav |
| 6,626,945 B2 | 9/2003 | Simon et al. |
| 6,679,917 B2 | 1/2004 | Ek |
| 6,706,005 B2 | 3/2004 | Roy et al. |
| 6,712,856 B1 | 3/2004 | Carignan et al. |
| 6,716,249 B2 | 4/2004 | Hyde |
| 6,772,026 B2 | 8/2004 | Bradbury et al. |
| 6,786,930 B2 | 9/2004 | Biscup |
| 6,855,150 B1 | 2/2005 | Linehan |
| 6,856,141 B2 | 2/2005 | Ariav |
| 6,932,842 B1 | 8/2005 | Litschko et al. |
| 6,944,518 B2 | 9/2005 | Roose |
| 6,984,993 B2 | 1/2006 | Ariav |
| 7,080,554 B2 | 7/2006 | Ariav et al. |
| 7,097,662 B2 | 8/2006 | Evans, III et al. |
| 7,190,273 B2 | 3/2007 | Liao et al. |
| 7,195,645 B2 | 3/2007 | Disilvestro et al. |
| 7,206,626 B2 | 4/2007 | Quaid, III |
| 7,239,908 B1 | 7/2007 | Alexander et al. |
| 7,275,218 B2 | 9/2007 | Petrella et al. |
| 7,383,164 B2 | 6/2008 | Aram et al. |
| 7,388,972 B2 | 6/2008 | Kitson |
| 7,410,471 B1 | 8/2008 | Campbell et al. |
| 7,427,200 B2 | 9/2008 | Noble et al. |
| 7,468,075 B2 | 12/2008 | Lang et al. |
| 7,534,263 B2 | 5/2009 | Burdulis, Jr. et al. |
| 7,618,451 B2 | 11/2009 | Berez et al. |
| 7,634,119 B2 | 12/2009 | Tsougarakis et al. |
| 7,634,306 B2 | 12/2009 | Sarin et al. |
| 7,842,092 B2 | 11/2010 | Otto et al. |
| 7,981,158 B2 | 7/2011 | Fitz et al. |
| 3,062,302 A1 | 11/2011 | Lang et al. |
| 3,066,708 A1 | 11/2011 | Lang et al. |
| 8,077,950 B2 | 12/2011 | Tsougarakis et al. |
| 8,108,190 B2 | 1/2012 | Riener et al. |
| 8,126,234 B1 | 2/2012 | Edwards et al. |
| 8,702,712 B2 | 4/2014 | Jordan et al. |
| 2002/0087274 A1 | 7/2002 | Alexander et al. |
| 2002/0099444 A1 | 7/2002 | Boyd et al. |
| 2002/0107522 A1 | 8/2002 | Picard et al. |
| 2003/0055502 A1 | 3/2003 | Lang et al. |
| 2003/0069591 A1 | 4/2003 | Carson et al. |
| 2003/0153978 A1 | 8/2003 | Whiteside |
| 2003/0216669 A1 | 11/2003 | Lang et al. |
| 2004/0009459 A1 | 1/2004 | Anderson et al. |
| 2004/0024311 A1 | 2/2004 | Quaid, III |
| 2004/0034272 A1 | 2/2004 | Diaz et al. |
| 2004/0034283 A1 | 2/2004 | Quaid |
| 2004/0034302 A1 | 2/2004 | Abovitz et al. |
| 2004/0098133 A1 | 5/2004 | Carignan et al. |
| 2004/0101866 A1 | 5/2004 | Nakashima et al. |
| 2004/0106916 A1 | 6/2004 | Quaid et al. |
| 2004/0133276 A1 | 7/2004 | Lang et al. |
| 2004/0138591 A1 | 7/2004 | Iseki et al. |
| 2004/0138754 A1 | 7/2004 | Lang et al. |
| 2004/0152970 A1 | 8/2004 | Hunter et al. |
| 2004/0162620 A1 | 8/2004 | Wyss |
| 2004/0230199 A1 | 11/2004 | Jansen et al. |
| 2004/0236424 A1 | 11/2004 | Berez et al. |
| 2004/0254771 A1 | 12/2004 | Riener et al. |
| 2005/0096535 A1 | 5/2005 | de la Barrera |
| 2005/0119661 A1 | 6/2005 | Hodgson et al. |
| 2005/0148843 A1 | 7/2005 | Roose |
| 2005/0154471 A1 | 7/2005 | Aram et al. |
| 2005/0170311 A1 | 8/2005 | Tardieu et al. |
| 2005/0197814 A1 | 9/2005 | Aram et al. |
| 2005/0209536 A1 | 9/2005 | Dariush |
| 2005/0234332 A1 | 10/2005 | Murphy |

(56) References Cited

U.S. PATENT DOCUMENTS

| | | |
|---|---|---|
| 2005/0251065 A1 | 11/2005 | Henning et al. |
| 2005/0267584 A1 | 12/2005 | Burdulis et al. |
| 2006/0029795 A1 | 2/2006 | Sawyer et al. |
| 2006/0030681 A1 | 2/2006 | Sawyer et al. |
| 2006/0095047 A1 | 5/2006 | de la Barrera |
| 2006/0133827 A1 | 6/2006 | Becouarn et al. |
| 2006/0142657 A1 | 6/2006 | Quaid et al. |
| 2006/0155380 A1 | 7/2006 | Clemow et al. |
| 2006/0190086 A1 | 8/2006 | Clemow et al. |
| 2006/0224088 A1 | 10/2006 | Roche |
| 2006/0235537 A1 | 10/2006 | Kuczynski et al. |
| 2007/0016329 A1 | 1/2007 | Herr et al. |
| 2007/0027631 A1 | 2/2007 | Cabrera et al. |
| 2007/0142761 A1 | 6/2007 | Kang et al. |
| 2007/0179626 A1 | 8/2007 | de la Barrera et al. |
| 2007/0219561 A1 | 9/2007 | Lavallee et al. |
| 2007/0219639 A1 | 9/2007 | Otto et al. |
| 2007/0233267 A1 | 10/2007 | Amirouche et al. |
| 2007/0296366 A1 | 12/2007 | Quaid et al. |
| 2008/0243127 A1 | 10/2008 | Lang et al. |
| 2008/0281328 A1 | 11/2008 | Lang et al. |
| 2008/0287962 A1 | 11/2008 | Dick et al. |
| 2009/0125117 A1 | 5/2009 | Paradis et al. |
| 2009/0131941 A1 | 5/2009 | Park et al. |
| 2009/0164024 A1 | 6/2009 | Rudan et al. |
| 2009/0264894 A1 | 10/2009 | Wasielewski |
| 2009/0306676 A1 | 12/2009 | Lang et al. |
| 2009/0313806 A1 | 12/2009 | Lang et al. |
| 2009/0326664 A1 | 12/2009 | Wagner et al. |
| 2009/0326665 A1 | 12/2009 | Wyss et al. |
| 2009/0326667 A1 | 12/2009 | Williams et al. |
| 2010/0009314 A1 | 1/2010 | Tardieu et al. |
| 2010/0016978 A1 | 1/2010 | Williams et al. |
| 2010/0016979 A1 | 1/2010 | Wyss et al. |
| 2010/0036500 A1 | 2/2010 | Heldreth et al. |
| 2010/0086181 A1 | 4/2010 | Zug et al. |
| 2010/0281678 A1 | 11/2010 | Burdulis, Jr. et al. |
| 2010/0303313 A1 | 12/2010 | Lang et al. |
| 2010/0303324 A1 | 12/2010 | Lang et al. |
| 2010/0305574 A1 | 12/2010 | Fitz et al. |
| 2010/0305907 A1 | 12/2010 | Fitz et al. |
| 2011/0039093 A1 | 2/2011 | Fukumura |
| 2011/0071528 A1 | 3/2011 | Carson |
| 2011/0071529 A1 | 3/2011 | Carson |
| 2011/0071530 A1 | 3/2011 | Carson |
| 2011/0071531 A1 | 3/2011 | Carson |
| 2011/0071532 A1 | 3/2011 | Carson |
| 2011/0071581 A1 | 3/2011 | Lang et al. |
| 2011/0087465 A1 | 4/2011 | Mahfouz |

FOREIGN PATENT DOCUMENTS

| | | |
|---|---|---|
| EP | 1208820 A2 | 5/2002 |
| EP | 1486900 A1 | 12/2004 |
| EP | 1762203 A2 | 3/2007 |
| WO | 1993025157 A1 | 12/1993 |
| WO | 1997023172 A2 | 7/1997 |
| WO | 199841152 A1 | 9/1998 |
| WO | 200041626 A1 | 7/2000 |
| WO | 2000059411 A1 | 10/2000 |
| WO | 200135872 A1 | 5/2001 |
| WO | 200170142 A1 | 9/2001 |
| WO | 2003030738 A1 | 4/2003 |
| WO | 2005039440 A2 | 5/2005 |
| WO | 2007139949 A2 | 12/2007 |
| WO | 2010120990 A1 | 10/2010 |
| WO | 2012021894 A2 | 2/2012 |
| WO | 2012021895 A2 | 2/2012 |

OTHER PUBLICATIONS

"Virtual", Merriam-Webster Online Dictionary, Merriam-Webster Online, Jul. 18, 2011, <http://www.merriam-webster.com/dictionary/virtual>.

Anderson, "Role of Rapid Prototyping in Preoperative Planning and Patient-Specific Implant Generation", Biomedical Engineering Conference, Proceedings of the 1996 Fifteenth Southern, 558-559, 1996.

Ateshian et al., "Quantitative Anatomy of Diarthrodial Joint Articular Layers", Basic Orthopaedic Biomechanics, 2d. Ed., pp. 253-273, 1997.

Biomet Orthopedics, Inc. Brochure "Patient-Matched Implants", 12 pages, Form No. Y-BMT-657/031500/M, 2000.

Birnbaum et al., "Computer-Assisted Orthopedic Surgery with Individual Templates and Comparison to Conventional Operation Method", Spine, 26(4), pp. 365-370, 2001.

Bono, "Digital Templating in Total Hip Arthroplasty", The Journal of Bone & Joint Surgery, 86-A(suppl. 2), pp. 118-122, 2004.

Cohen et al., "Computer-Aided Planning of Patellofemoral Jount OA Surgery: Developing Physical Models from Patient MRI", Medical Image Computing and Computer-Assisted Intervention—MICCAI '98 Lecture Notes in Computer Science, 1496, 9-20, DOI:10.1007/BFb0056183, 1998.

Colwell et al., "The Electronic Knee", Total Knee Arthroplasty: A Guide to Get Better Performance, Springer, J. Bellemans et al., Editors, Chapter 45, pp. 282-287.

Heinlen et al., "An Instrumented Knee Endoprosthesis for Measuring Loads in Vivo", Scientific Poster presented at the 51st Annual Meeting of the Orthopaedic Research Society, Washington, D.C., Feb. 20-23, 2005.

Insights Dassault Systems Realistic Simulation Magazine, "Smith & Nephew Improves its Knee Replacements", DS Simulia, pp. 1-28, Sep./Oct. 2010.

International Search Report and Written Opinion dated Mar. 27, 2012 in related Application No. PCT/US2011/047775.

International Search Report and Written Opinion dated Mar. 27, 2012 in related Application No. PCT/US2011/047784.

Jim X. Chen et al., "Knee Surgery Assistance: Patient Model Construction Motion Simulation, and Biomechanical Visualization", IEEE Transactions on Biomedical Engineering, vol. 48, No. 9, Sep. 2001, pp. 1042-1052.

Kshirsagar et al., "Measurement of Localized Cartilage Volume and Thickness of Human Knee Joints by Computer Analysis of Three-Dimensional Magnetic Resonance Images", Investigative Radiology, 33(5), pp. 289-299, 1998.

Kwak et al., "An Anatomically Based 3-D Coordinate System for the Knee Joint", 1995 Advances in Bioengineering, BED-31, pp. 309-310, 1995.

McKinnon et al., "The Virtual Knee", Total Knee Arthroplasty: A Guide to Better Performance, 2005, pp. 159-162, Springer Medzin Verlag, Heidelberg, GermanyKinematics, Chapter 24.

Morris et al., "e-knee: Evolution of the Electronic Knee Prosthesis: Telemetry Technology Development", The Journal of Bone & Joint Surgery, vol. 83-A, Supplemental 2, Part 1, 2001.

Peterfy, "MRI in the Assessment of Synovium and Cartilage", British Journal of Rheumatology, 35(suppl. 3), pp. 3-5, 1996.

Popovic et al., "Modeling of Intensity for Knowledge-Based Level Set Algorithm in Calvarial Tumors Segmentation", R. Larsen, M. Nielsen, and J. Sporring (Eds.), MICCAI 2006, LNCS 4191, pp. 864-871, 2006.

Portheine, "CT-Based Planning and Individual Template Navigation in TKA", Navigation and Robotics in Total Joint and Spine Surgery, Chapter 48, pp. 336-342, 2004.

Portheine, "Modellierung Von Bandstrukturen Bei Der CT-Bild-Basierten Planung Knieendoprothetischer Eingriffe", Biomedizinische Technik, Band 47, Erganzungsband 1, Teil 1, pp. 53-56, 2002.

Radermacher et al., "Computer Assisted Orthopedic Surgery with Image Based Individual Templates", Clinical Orthopaedics and Related Research, 354, pp. 28-38, 1998.

Radermacher et al., "CT Image-Based Planning and Execution of Interventions in Orthopedic Surgery Using Individual Templates—Experimental Results and Aspects of Clinical Applications", In Nolte, LP, Ganz R (eds), CAOS—Computer Assisted OrthopaedicSurgery, Bern, Hans Huber, pp. 42-52, 1998.

Radermacher, "Computerunterstutzte Operationsplanung und—ausfuhrung mittels individueller Bearbeitungsschablonen in der

(56) References Cited

OTHER PUBLICATIONS

Orthopadie", Helmholtz-Institut fur Biomedizinische Technik an der RWTH Aachen, Shaker Vortag, D82, pp. 1-234, 1999.
Radermacher, "Computerunterstutzte Operationsplanung und—ausfuhrung mittels individueller Bearbeitungsschablonen in der Orthopadie—Computer aided planning and execution of surgery by means of individual processing templates in orthopedics",Section 4.2 of the doctoral thesis of Klaus Rademacher, M/PLU-VARIA, 5 pages.
Recht et al., "MR Imaging of Articular Cartilage: Current Status and Future Directions", AJR, 163, pp. 283-290, 1994.
Recht et al., "MRI of Articular Cartilage: Revisiting Current Status and Future Directions", AJR Musculoskeletal Imaging Review, 185, pp. 899-914, 2005.
Schkommodau et al., "Genauigkeitsuntersuchung Zur Mechanischen Steifigkeit Kes C-Bogens Bei Navigationsaufgaben", Biomedizinische Technik, Band 47 Erglinzungsband 1, Teil 1, pp. 41-43, 2002.
Staudte, "Computergestutzte Operations-planung und—technik in der Orthopadie", Nordrhein-Westfalische Akademie der Wissenschafter, Vortage N444, 2000.
Staudte, "Computerunterstutzte Operationsplanung und—technik in der Orthopadie", 416th Meeting on Jan. 10, 1996 in Dusseldorf, M/PLU-VARIA, 3 pages, 2010.
Techmedica Brochure on Bone Modeling/Custom Prosthesis/Bone Staple System, Bulletin No. 1004, 10 pages, 1982.
Townsend et al., "Micro Datalogging Transceiver Networks for Dynamic Activity & Structural Performance Monitoring," Microstain Presentation from www.microstain.com, Date unknown but probably in the 2001 to 2003 timeframe. 1999-2007, according towww.microstain.com.
U.S. Appl. No. 10/146,862, filed May 15, 2002 (abandoned).
Wu et al., "Anatomically Constrained Deformation for Design of Cranial Implant: Methodology and Validation", R. Larsen, M. Nielsen, and J. Sporring (Eds), MICCAI 2006, LNCS 4190, pp. 9-16, 2006.
Zimolong, "Untersuchung Adaptiver Planungsmodellezur Osteo-Synthese Der Schenkelhalsfraktur", Biomedizinische Technik, Band 47, Erganzungsband 1, Teil 1, pp. 93-96, 2002.

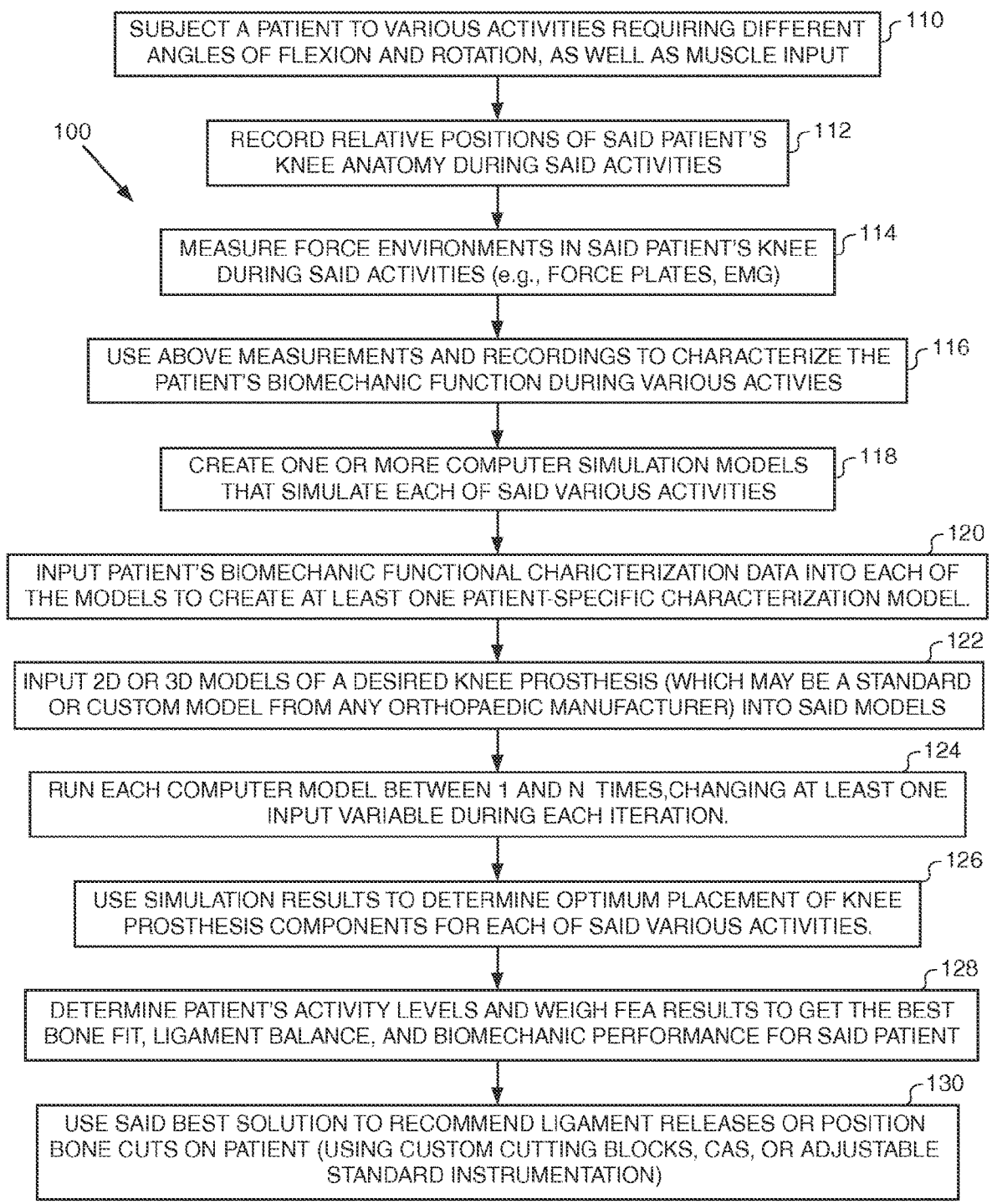

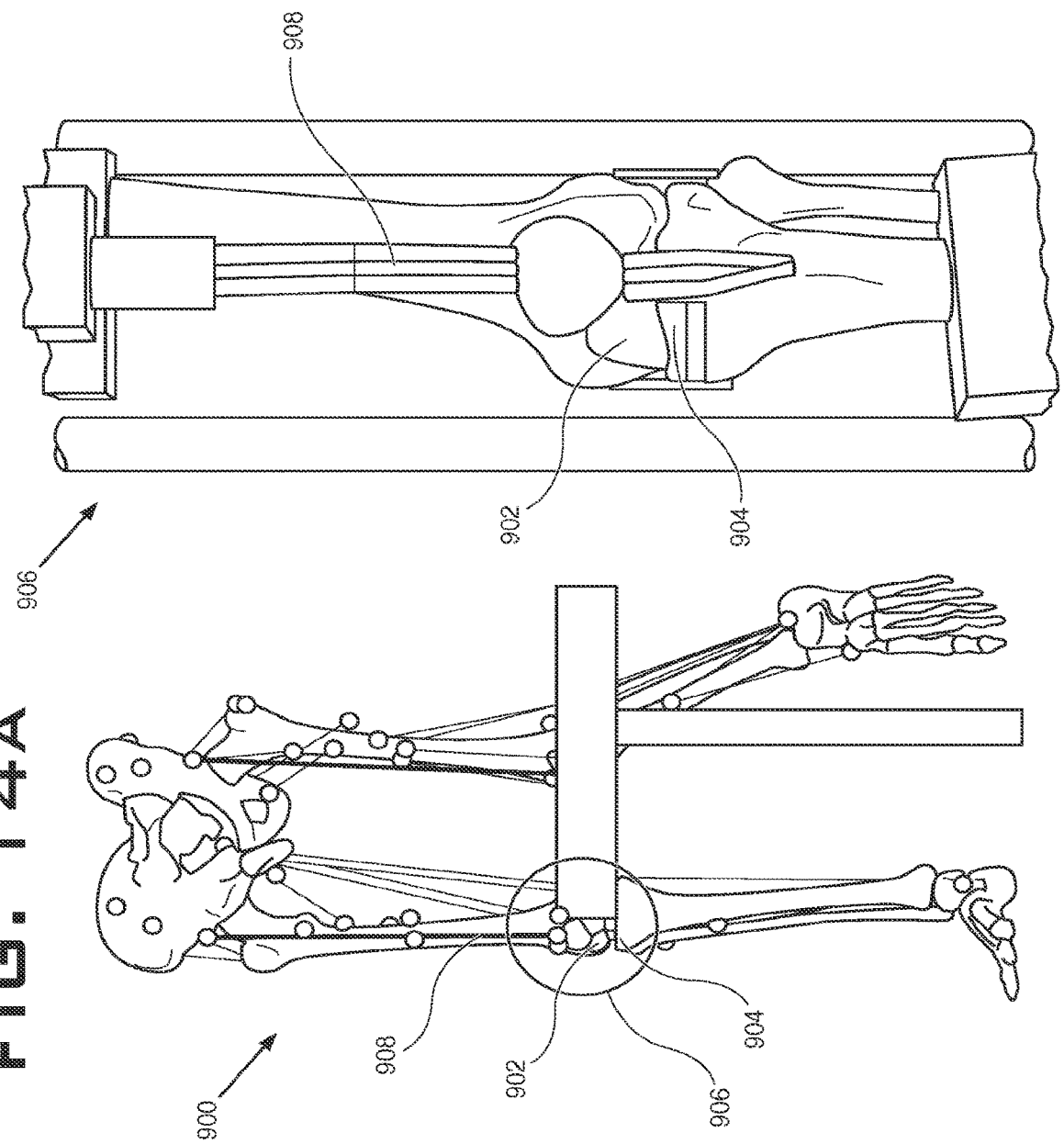

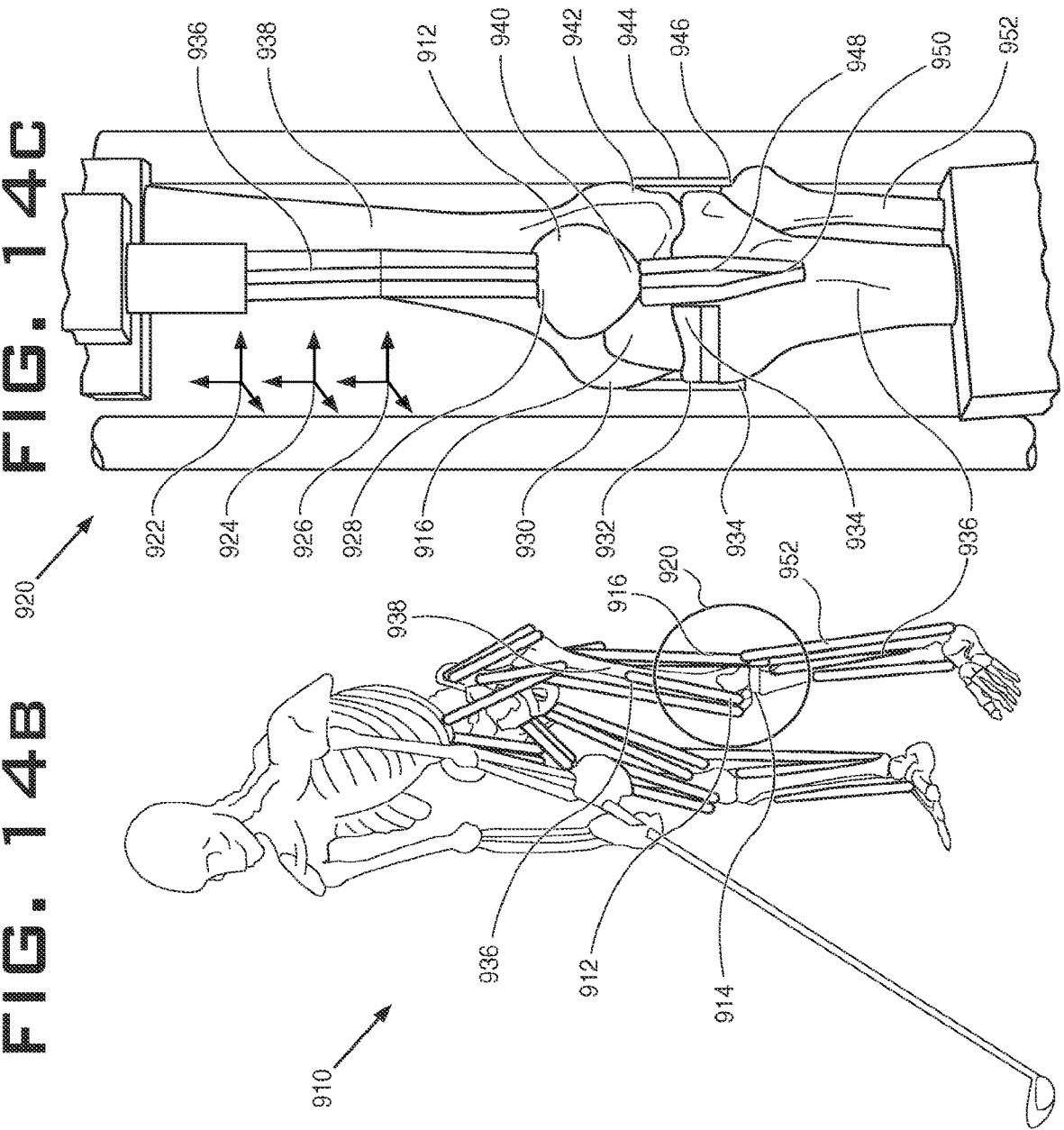

OPERATIVELY TUNING IMPLANTS FOR INCREASED PERFORMANCE

CROSS-REFERENCE TO RELATED APPLICATIONS

This application is a continuation of U.S. patent application Ser. No. 15/088,697, filed on Apr. 1, 2016, now U.S. Pat. No. 10,600,515 issued Mar. 24, 2020, which is a continuation of U.S. patent application Ser. No. 13/951,009, filed on Jul. 25, 2013, which is a continuation of U.S. patent application Ser. No. 13/302,256, filed on Nov. 22, 2011, now U.S. Pat. No. 8,521,492 issued Aug. 27, 2013, which is a continuation of U.S. patent application Ser. No. 12/234,444, filed on Sep. 19, 2008, now U.S. Pat. No. 8,078,440 issued Dec. 13, 2011, each of which is hereby incorporated herein by reference in its entirety.

BACKGROUND OF THE INVENTION

Field of the Invention

The present invention relates generally to optimizing implant position during total knee arthroplasty (TKA), and more particularly to a novel method of preoperatively characterizing an individual patient's biomechanic function in order to optimize the orientation of components of a knee prosthesis.

Related Art

Software programs which simulate in-vivo functional activities (e.g., LifeMOD™/KneeSIM a product of LifeModeler®, Inc. San Clemente, Calif.), have been used for the purpose of evaluating the performance of implant designs. Such programs use a three-dimensional, dynamics-oriented, physics-based modeling methodology. While these programs have been used to design implant geometries in the past, the prior art has not utilized such software to fine-tune the anatomical placement of implants (i.e., standard and custom) so that they meet and exceed an individual patient's needs.

Many times in total knee arthroplasty (TKA), poor post-operative patient outcomes are not caused from a poorly-designed prosthesis. Instead, the problem may often stem from a well-designed prosthesis being installed in a less-than-optimal biomechanic position relative to the natural anatomy of the patient in an attempt to get the best anatomic fit. In other words, the probability of revision knee surgery due to pain or abnormal wear may be high even with a well-designed knee-prosthesis, if said prosthesis is misaligned or if said prosthesis is installed without considering the biomechanic effects of prosthetic orientation.

Conventionally, knee prosthetic components are pre-operatively sized and positioned based on static anterior-posterior and/or sagittal X-ray templates in fall extension. Range of motion (ROM) and joint stability is assessed with the patient under anesthesia, and so any pain front over-stressing or impinging soft tissue that might result from surgery (for example, pain associated with "stuffing the patella" or "stuffing the flexion-extension gap") cannot be determined until the patient recovers and discovers an unwanted or unnatural post-operative feeling.

The present invention aims to solve the problems encountered in the past by providing alternative preoperative and intra-operative "templating" method steps which give significant weight to soft tissue balancing and patient biomechanic function, in order to anticipate and optimize dynamic interactions with chosen implanted devices. In doing so, a surgeon is armed with more information during intra-operative positioning of the implanted devices and can expect more favorable patient outcomes more often. The present invention more specifically aims to solve the problems encountered by the prior art by using a means for knee prosthesis templating which is more dynamic than a static X-ray at full extension.

SUMMARY OF THE INVENTION

The aforementioned needs are satisfied by several aspects of the present invention.

According to one aspect of the invention, there is provided a method of preoperatively characterizing an individual patient's biomechanic function, in order to optimize the orientation of one or more prosthesis components prior to implantation of said one or more prosthesis components. The method generally includes the steps of: subjecting a patient to various activities; recording relative positions of anatomy during said various activities; measuring force environments within said patient's anatomy and affected area during said various activities, characterizing the patient's biomechanic function from said relative positions and corresponding force environments; inputting the measured force environments, relative positions of knee anatomy, and patient's biomechanic function characterization into one or more computer simulation models—each computer simulation model corresponding to at least one of said various activities; inputting a 2D or 3D computer model of said one or more desired prosthesis components (which may be standard prosthesis components or custom prostheses components) into said one or more computer simulation models; iteratively running each of said one or more computer simulation models while changing at least one input variable between iterations; determining from said computer simulation models, one or more preferred placements for each of said one or more prosthesis components for the particular patient; suggesting or recommending said preferred placements to a surgeon; receiving input from the surgeon, who may decide to compromise between good anatomic fit and good biomechanic performance; optionally altering said one or more optimal placements for each of said one or more prosthesis components according to surgeon input; and providing a means for implanting said one or more prosthesis components in said corrected preferred placement.

Where used herein, the term "biomechanic" broadly encompasses all things relating to kinematics and kinetics of the body. In physics, kinetics may be described as a branch of dynamics concerning motions of bodies which are produced under certain force environments. "Kinetic" where used herein, suggests one or more forces, loads, strains, moments, or stresses. Kinematics may be described as is the study of motion of objects and how the motion affects force environments. "Kinematic" where used herein, suggests one or more ranges of motion, translations, movements, angulations, or rotations.

Also, where used herein, the term "anatomic fit" broadly encompasses considerations of: 1) resection efficiency (i.e., minimizing bone loss for the patient given a particular prosthesis geometry), 2) interface fit (i.e., how well the prosthesis adheres to bone and how robust the prosthesis is to cement interface shear loading given a large range of spatial orientations and/or bone interface geometries), and 3)

bone coverage/fit (i.e., how well the prosthesis covers bone without overhanging or under-hanging which could cause soft-tissue impingement)

According to another aspect of the present invention, a surgical method is provided. The surgical method comprises the step of determining a relationship between a first prosthetic component and a second prosthetic component based at least in part on information acquired about said first prosthetic component and information acquired about the second prosthetic component.

According to yet another aspect of the present invention, a surgical method is provided. The surgical method comprises planning either preoperatively, or intra-operatively, the placement of at least a second prosthetic component within a selected joint, based at least in part on 1) information acquired about a first prosthetic component and 2) a desired relationship between said first and second prosthetic components.

According to even another aspect of the present invention, there is provided a surgical system that includes a means for computer simulation which is configured to determine at least one of a spatial relationship, anatomic relationship, biomechanic relationship, geometric relationship, and a size relationship between a first prosthetic component and a second prosthetic component based at least in part on a first feature of said first prosthetic component and a second feature of said second prosthetic component.

According to another aspect of the present invention, there is provided a computer programmed with software that virtually or actually evaluates a functional relationship between a first prosthetic component and a second prosthetic component based on at least one input condition.

According to yet other aspects of the present invention, there is provided a surgical method which involves the step of relating a first feature of a first prosthetic component to a second feature of a second prosthetic component, and modifying one or more relationships therebetween based on a performance characteristic (i.e., implant "tuning").

The present invention serves to increase functional performance (e.g., biomechanic function), increase durability (e.g., reduce wear), reduce or eliminate abnormal motion (e.g., paradoxical motion), and create a more natural postoperative feeling (e.g., improved proprioception) for said individual patient. By measuring, interpreting, and understanding the preoperative biomechanic characteristics of a patient's knee or other joint, computer simulation models can assist a surgeon by providing one or more suggested surgical plans along with expected performance results corresponding to each of said one or more suggested surgical plans. Such surgical plans may generally provide suggestions for optimizing implant sizing, varus/valgus cut angle, posterior slope cut angle, internal/external rotational positioning angle, cut depth, anterior/posterior cut locations, flexion/extension cut angle, and medial/lateral positioning of a selected prosthesis so as to optimize ligamentous or other soft tissue releases. The computer simulation models may further assist the surgeon in selecting one or more proper prosthetic components from any given number of standard or custom prosthesis designs from one or more orthopedic manufacturers.

It is anticipated that by utilizing the method steps provided by the present invention, final positioning of a knee prosthesis within the patient's joint is optimized to reduce quadriceps misfire and strain, reduce implant loosening and subluxation, maintain balanced soft-tissue envelopes, reduce implant wear (by positioning implant components in such a way that magnitudes and directions of frictional forces experienced during a patient's typical biomechanic functions are minimized), reduce or eliminate abnormal motion, and give the patient a more natural postoperative feeling.

FIG. 13 is a Venn diagram (800) illustrating problems encountered by prior art surgical methods. The diagram (800) comprises at least three prosthetic performance circles (802, 804, and 806). Performance circle (802) is representative of best anatomic fit for a given prosthesis. Ligament balance performance circle (804) is representative of best intra-operative ligament balancing that can be achieved without patient muscle input and other dynamic input. For instance, a good flexion/extension gap and good stability during trial reduction in TKA might place an overall prosthesis performance value (812) within the ligament balance performance circle (804).

Performance circles (806, 806', 806", 806''') are representative of the best expected biomechanic performance during various postoperative activities. Biomechanic performance circles (806, 806', 806", 806''') may move relative to the other performance circles (802, 804) or may become larger or smaller depending on: 1) how robust the prosthesis is to mis-implantation, 2) how well the prosthesis geometries address all patients (including outliers) within a patient population, and 3) the activity from which performance is measured and based.

Conventionally, a surgeon selects a prosthetic component type and size that anatomically fits a patient the best, and then implants the prosthetic component in an orientation for best bony coverage and anatomic fit (e.g., in good mechanical axis alignment). The overall performance achieved from a prosthesis installed in such a way may be characterized as having a marginal or good overall prosthesis performance value (810). Overall prosthesis performance values (810) achieved purely based on good anatomical fit (802) are limited because: 1) flexion/extension gaps may not be optimized and may lead to unwanted laxity or stiffness throughout portions of a range of motion, 2) ligaments may not be balanced which may lead to pain or compensations during movement, and 3) prosthesis surface geometries are inherently compromised because they are designed to suit a large patient population and may insufficiently address the needs of every patient (e.g., "outliers").

In total knee arthroplasty, a surgeon has the option of changing tibial insert thicknesses and/or performing ligamentous releases in order to obtain a good overall prosthesis performance value (812) for both anatomic fit (802) and intra-operative ligament balance (804). However, since patients are unconscious during trial reduction, the surgeon has no good way of knowing what the actual biomechanic performance (806) of the artificial knee will be during everyday active use, when muscles are firing and loads and other stresses are applied to the implant, bone, and surrounding soft tissues. Moreover, even though ligament releases can be used to obtain good intra-operative ligament balance (804), there is a possibility that the releases will not yield acceptable or optimal biomechanic results (806) during physical activities by the patient after post-operative recovery.

It is therefore a goal of the present invention to help a surgeon determine how to implant one or more prosthetic components of a prosthesis in order to get the best overall anatomic fit (802), intra-operative ligament balance (804), and postoperative biomechanic performance (806) simultaneously, as indicated by the overall prosthesis performance value (814). Overall prosthesis performance value (814) is exemplary of a prosthetic configuration which is sized and spatially oriented so that it achieves good anatomic fit (802), as well as provides good intra-operative ligament balance (804) and good postoperative biomechanic function (804) during dynamic activities routinely performed by the patient.

It is also a goal of the present invention to enable a surgeon to make the best possible compromises between anatomic fit (802), intra-operative ligament balance (804), and postoperative biomechanic function (806) in situations when all three performance characteristics (802, 804, 806) cannot be achieved simultaneously. For instance, for some prosthetic implants, computer simulations may indicate that good biomechanic performance (806") will not yield good anatomic fit (802). In such instances, the surgeon may have to give up some biomechanic performance (806") for better anatomic fit (802), or select a different prosthetic implant which is more robust and/or suitable for the patient.

Further areas of applicability of the present invention will become apparent from the detailed description provided hereinafter. It should be understood that the detailed description and specific examples, while indicating certain embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the present invention and together with the written description serve to explain the principles, characteristics, and features of the invention. In the drawings:

FIG. 1 is a flowchart generally describing a method for determining optimal placement of a knee prosthesis for an individual patient according to some embodiments of the present invention;

FIGS. 14a-c illustrate 3D computer simulation models according to some embodiments of the present invention.

DETAILED DESCRIPTION OF THE EMBODIMENTS

Figure 2A:
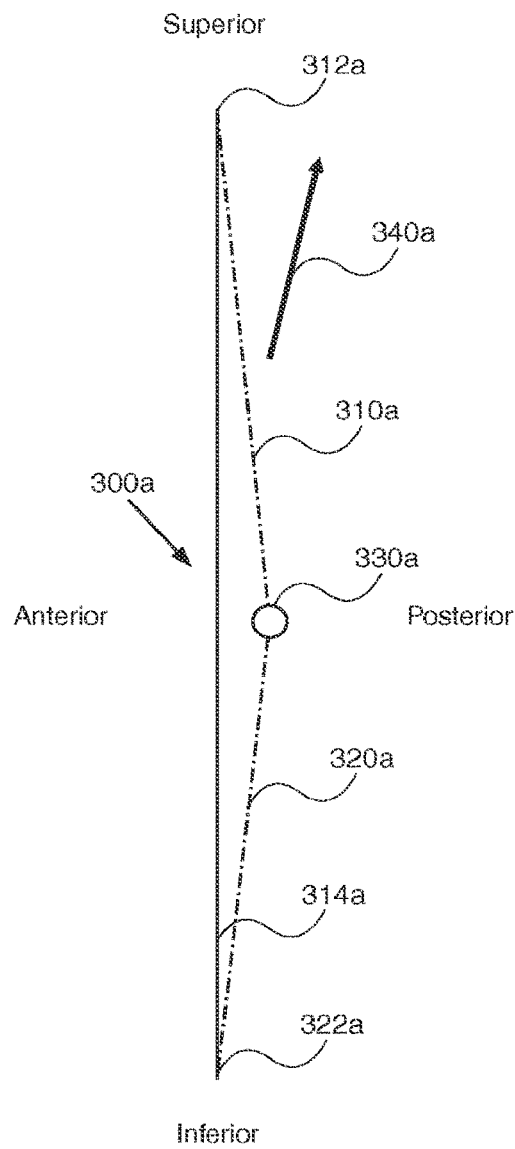
FIG. 2a. is a schematic diagram illustrating a side view of a normal knee or a good postoperative knee and its kinetic function at screw-home position and full-extension.

The following description of the preferred embodiments is merely exemplary in nature and is in no way intended to limit the invention, its application, or uses.

The invention provides, in part, a method for preoperatively characterizing an individual patient's biomechanic function in order to optimize the placement orientation of one or more knee prosthesis components within an individual patient's anatomy.

It is preferred that the preoperative characterization be done in a way that is efficient and effective, and that the characterization be based on accurate simulations of the most routine activities performed by the individual patient. In other words, for less-active patients, characterization may be performed by measuring biomechanics during simple chair rises, squatting, and static standing activities (as shown in FIG. 14a). Alternatively, for younger, more active patients, characterization may be done by measuring patient biomechanics during mock golf swings (as shown in FIG. 14b), jogging, biking, swimming, or stair-climbing activities. Any means for measuring may be used and may include without limitation: gait lab equipment, cameras, fluoroscopy, position markers, accelerometers, strain gauges, piezoelectric devices, force sensors, transducers, position sensors, servo devices, computer-assisted-surgery (CAS) devices, infrared devices, force plates, electromyography (EMC) devices, neuromuscular measuring devices, and current, voltage, or electrical power measuring instruments.

It should be understood that the usefulness of the present invention is not limited to total knee arthroplasty (TKA) applications. Rather the methods of the present invention may serve as well in knee hemi-arthroplasty, knee resurfacing, knee uni-compartmental arthroplasty, knee bi-compartmental arthroplasty, total hip arthroplasty (THA), hip hemi-arthroplasty, hip resurfacing, shoulder arthroplasty, shoulder hemi-arthroplasty, elbow reconstruction, ankle reconstruction, and other surgical applications. In such non-TKA cases, biomechanic function measurements and modeling can be adjusted to better reflect activities using the affected joint. For example, in shoulder surgery, the biomechanics of a patient may be measured during and/or modeled for throwing an object, lifting an object over the head, totaling a steering wheel, opening a door, or paddling a kayak. In another example, for hip resurfacing procedures, the biomechanic function of a patient may be measured during and/or modeled for bicycle riding, kicking a soccer ball, and/or sitting cross-legged, along with other activities involving the hip joint, in yet another example, for elbow reconstruction, the biomechanics of a patient may be measured during and/or modeled for repetitive tennis or golf swings.

FIG. 1 is a flowchart briefly illustrating several method steps according to some embodiments of the present invention. The method (100) begins with subjecting a patient to various activities (110) involving the affected joint. Said activities may require different levels of muscle input, muscle control, angles of leg flexion/extension, and angles of internal/external rotation. The activities may include without limitation: normal erect walk, chair rise, chair sit, stair climb, stair descend, static stand at full extension, squat, golf swing (as shown in FIG. 14b), preferred prayer stance, jog, kneel, power walk, pivot turn, and bike, among others. Ideally, the activities chosen for biomechanic function characterization are activities which are most preferred by the patient. For instance, if the patient indicates that he or she spends much time kneeling for prayer, squatting during gardening, playing golf, sitting, or has a job that requires excessive standing or walking, overall patient satisfaction will be largely based on the biomechanic performance of the implant during the patient's routine activities.

Once the appropriate activities which best suit an individual patient's needs are selected, position and force measurements are taken at different leg position intervals throughout ranges of motion for at least one of said activities (112, 114). For instance, a patient may be measured and digitized utilizing any one or more of gait lab equipment, fluoroscopy equipment, cameras, position markers, lower extremity motion capture, anthropometries, radiological scans (e.g., CT, MRI), accelerometers, strain gauges, electromyography (EMG), piezoelectric devices, transducers, force sensors, position sensors, infrared, magnetic fields, signal triangulation, RFID, biodex balance characterization, radio waves, computer-assisted-surgery (CAS) devices, 3D imaging systems, radiostereometric analysts (RSA) devices, and force plates, in order to characterize the biomechanics within a patient's knee during said activities. Additionally, at any time during each of the activities, a patient may indicate a pain value or make other observations to further characterize him/herself during said activities. Indicating pain level at different positions during an activity may clarify why certain functional patterns are exhibited. Pain level during the activities may be indicated by the patient incrementally on a scale from one to ten throughout the activity or other pain scales may be advantageously utilized. Alternatively, pain medication and/or anti-inflammatories may be administered to the patient prior to characterization steps (110) and (112) so that the patient's movements are not compromised by pain and swelling experienced during the measured activity.

Once data is collected from the patient using the above-mentioned methods, a patient's biomechanic function is characterized (116). Functional characterization (116) may be patient-specific, or it may be generalized to fall within one or more predetermined categories of patient functional envelopes (e.g., minor pronation, major pronation, severe valgus, flat footed, tip-toed, etc). It is preferred that characterization (116) of the patient's biomechanic function is done in as much or as little detail as is necessary to correctly orient one or more prosthetic components so that the one or more prosthetic components yield the best possible performance characteristic in any one or more of the categories of long-term or short-term wear ($mm^3$ per million cycles), stress, range of motion (ROM), kinematics (e.g., tibiofemoral and patellofemoral interactions, maximum anterior-posterior translation, maximum flexion, maximum internal/external tibial or femoral rotation, maximum patella flexion, maximum patella tilt, maximum patella spin, maximum femoral rollback), kinetics (e.g., optimizing compressive forces, shear forces, torque, anterior-posterior forces, medial-lateral forces, and flexion moments acting on implant components), biomechanics, implant robustness, fatigue life, fixation strength, shear loading at cement or ingrowth interface, bony impingement, soft-tissue impingement, joint laxity, subluxation, subsidence, ligament balancing, ligament force, quadriceps force, knee efficiency, patellar femoral impingement, Q-angle, stability, anatomic fit (e.g., bone fit), implant longevity, and natural postoperative feeling (e.g., good proprioception).

Once the individual patient's functional biomechanic pattern or patterns are characterized, one or more values representative of patient characteristics may be loaded into one or more computer simulation models. Computer simulation models may be generic and modified for each patient, or the computer simulation models may be created from scratch (118) specifically from the patient's functional characterization and measurements gathered from the patient in method steps (110), (112), and (114). The computer simulation models may be facilitated by proprietary software or commercially available off-the-shelf software such as LifeMOD™ KneeSIM or LifeMOD™ BodySIM software, available from LifeModeler®, Inc. San Clemente, Calif. The computer simulation models may be separated by activity (i.e., one model for simulating stair climb, and another model for simulating chair rise), or the simulation models may be combined and spliced into a single sequential computer simulation model (e.g., a model simulating a patient starting with a chair rise, then transitioning to stair climb, then transitioning to a squat sequence, then transitioning to a kneeling sequence, then transitioning to a walking sequence, and then finishing with a chair sit). The computer simulation models may be custom-designed from scratch and therefore, entirely made, specific to the individual patient, or the models may be patient-approximated by inputting patient characteristics and patient data into existing universal models. Alternatively, the simulation models may be designed from large databases of previously characterized patient groups. In one example, a database may have four different computer simulation models for the same walking activity: one for pronated patents, one for flat-footed patients, one for severe valgus patients, and one for severe varus patients. An individual patient's biomechanic data is inputted into the simulation model that is most representative of the patient, in some embodiments, a simulation model such as the one illustrated in FIG. 9 may be used to create a data array of expected patient results, and then, using a program such as Minitab® statistical software, said expected patient results can be compared with a lookup table that outlines recommended implant configurations for corresponding expected patient results. All computer simulation models described herein may be adjusted to better simulate, the characterized biomechanic function of an individual patient (120) in ways other than what is explicitly disclosed.

The method (100) of the present invention may further include method step (122). This step (122) comprises inputting a desired knee prosthesis product make and model) number into a computer simulation model, said model simulating the individual patient's functional patterns or patterns very similar to those of the patient. The desired knee prosthesis may include without limitation, any one or more of a unicondylar femoral component, a patello-femoral component, a bi-compartmental femoral component, multiple unicondylar femoral components, a bi-compartmental femoral component in combination with a unicondylar femoral component, two unicondylar femoral components in combination with a patello-femoral component, a unicondylar tibial insert, a unicondylar tibial tray, a total bi-condylar cruciate-sparing tibial insert, a bi-condylar cruciate-sparing tibial tray, a bi-condylar cruciate-sacrificing tibial insert, a bi-condylar cruciate-sacrificing tibial tray, a patellar button, a patellar tray, fixed-bearing devices, mobile-bearing devices, total arthroplasty devices, hemi-arthroplasty devices, and combinations thereof. The step (122) of inputting the desired knee prosthesis make and model number can be facilitated by a database of CAD files obtained from one or more orthopaedic manufacturers or third parties and stored on a server drive, or the like. If custom prostheses are used, entire CAD files of the custom knee prosthesis to be implanted may be uploaded manually into the computer simulation model. The knee prosthesis CAD models imported into the computer simulation model may be two-dimensional (2D) models or three-dimensional (3D) models. The knee prosthesis models may be imported into a computer simulation model without specifying prosthetic component sizes, so that the computer simulation model can suggest an optimum size for each prosthetic component in addition to one or more optimum orientations corresponding to said optimum size.

For instance, a smaller-sized prosthetic component positioned in a first optimal orientation may yield better biomechanic performance (806) as compared with a larger-sized prosthetic component in a second optimal orientation. In other instances, for example, computer simulation modeling according the present invention may indicate that a size large patello-femoral component implanted in a first configuration with respect to a size small medial unicondylar femoral component will yield the same or better performance characteristics for a given activity than a size small patello-femoral component implanted in a second configuration with respect to a size small unicondylar femoral component. Performance differences may be attributed to the tangency and transition between the patello-femoral component and the unicondylar femoral component. This information can be relayed to the surgeon before or during surgery. Using anatomic landmarks and measurement data (e.g., as shown in FIGS. 3-7) gathered during patient characterization (112, 116), either a computer simulation model or a CAS system can help the surgeon determine which relationships would yield the best anatomic fit with no substantial decrease in biomechanic performance.

The computer simulation models of the present invention generally simulate patient-specific biomechanic patterns for one or more various activities and may be iteratively run for a finite number of modeling iterations (124). During each modeling iteration (124), one or more input variables are incrementally changed or added according to the patient's functional characterization and functional envelope. Certain input variables may be given more weight and importance depending on the individual patient's needs and expectations. Input variables that are changed or added within the computer simulation models during each modeling iteration may include, for instance, the make and model of the desired implant, the size of each component of the desired implant, the anterior-posterior (A-P) positioning of each component of the desired implant, the medial-lateral (M-L) positioning of each component of the desired implant, the superior-inferior (S-I) positioning of each component of the desired implant, the internal-external rotation positioning of each component of the desired implant, the varus-valgus (i.e., abduction-adduction) positioning of each component of the desired implant, and the flexion-extension positioning of each component of the desired implant. It is to be understood that one of ordinary skill in the art would appreciate that many other input variables could be added or changed in the computer simulation models.

After the computer model simulations are completed, the software program, or a program separate from the software program compiles the expected biomechanic results for different implant configurations. Results may come in the form of tables of raw data corresponding to magnitudes and directions of force vectors, loads, shear stresses, and moments experienced by one or more of the implant components during each simulation iteration. Raw data may be stored in a database for subsequent implant design studies or to help create the characterization chart or lookup table mentioned later in this disclosure. Alternatively, raw data may be processed for clearer user analysis and interpretation by the surgeon. The data may even be distributed to the patient, as a means of documenting and communicating the expected overall prosthesis performance of their artificial knee after it is implanted in them. The results are compiled and processed in order to determine the optimum positioning and sizing information for each knee prosthesis component (126), relative to the patient's anatomy. For instance, the computer simulation models described may export the raw data from iterative computer simulations into a data program preferably configured for statistical analysis (e.g., Microsoft™ Excel™ or MATLAB® by The MathWorks™ Inc.). Then, the data program itself or another program linked thereto compiles the raw data and determines one or more optimal values for each input variable used in the iterative computer simulations (128). Knowing the optimal values for each input variable of the simulations (128) will help a surgeon formulate a surgical plan specific to the measured patient. The surgical plan might include suggestions for strategically orientating bony cuts, holes, and ligamentous releases so as to provide optimum stresses and forces on the implant and surrounding soft tissues. Surgical recommendations and/or the expected biomechanic results may be presented to a surgeon or engineer by means of charts (as shown in FIGS. 15a-f), graphs, spreadsheets, or tables. Such means is generated by the data program or the simulation software itself. For instance, after iterative modeling, computer simulation software may indicate: 1) the best prosthesis component sizes to use, 2) the best anterior-posterior (A-P) slope angles to use for each prosthesis component, 3) the best medial-lateral (M-L) orientations for each prosthesis component relative to bony anatomy, 4) the best superior-inferior (S-I) position for each prosthesis component (i.e., depth of proximal or distal bone cuts), 5) the best internal-external rotation position for each component of the prosthesis, 6) the best varus-valgus (i.e., abduction-adduction) angles to use for each prosthesis component, and 7) the best flexion-extension angles for each component of the prosthesis.

The computer simulation models may take into consideration stresses in the medial and lateral collateral ligaments (MCL, PCL), anterior cruciate ligament (ACL), posterior cruciate ligament (PCL), quadriceps muscle, patellar tendon, medial and lateral retinaculae, and other soft tissues during iterative simulation, and may, without limitation, suggest any one or more of: ligament release locations and amounts (e.g., depth of incision), prosthetic component orientations, and bone cut configurations dial will provide the most stability and lowest forces at the implant-bone interfaces.

FIG. 2a. illustrates a side view of a normal knee (300a) at screw-home position while standing in full-extension. The mechanical axis (314a) of the leg extending from the femoral head center (312a) to the ankle center (322a) is generally located very slightly anterior to the knee center (330a). The femoral anatomic axis (310a) and the tibial anatomic axis (320a) are in slight hype rex tension so to form a toggle-like screw-home position that reduces necessary quadriceps activation (340a) while standing. It is an object of the present invention to use computer modeling to ensure that knee prosthesis components are placed such that the mechanical axis passes very slightly in from of the knee center (330a) when in full-extension. This ensures a stable screw-home position without excessive quadriceps muscle-firing (340a), individual patient biomechanic function characterization and computer simulation prior to surgery may allow fine-tuning of the screw-home position to create the most natural feeling possible with any given artificial knee, and replicate the kinematic function of a normal knee (FIG. 2a).

Figure 2B:
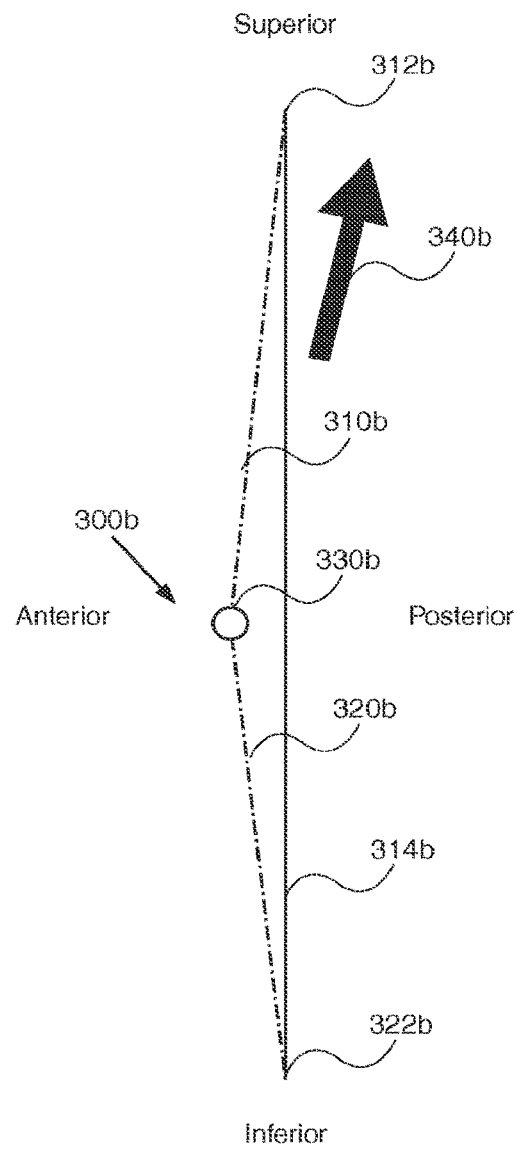
FIG. 2b. is a schematic diagram illustrating a side view of a deficient postoperative knee and its kinetic function at screw-home position and full-extension.

FIG. 2b. illustrates a side view of a deficient postoperative knee (300b) at screw-home position while standing in full-extension. The mechanical axis (314b) of the leg extends from the femoral head center (312b) to the ankle center (322b) and is generally located slightly posterior to the knee center (330b). The femoral anatomic axis (310b) and the tibial anatomic axis (320b) are in slight flexion creating an unstable screw home position that requires quadriceps activation (340b) in order to maintain stability while standing in extension. This will create a sense of instability and non-natural feeling in the joint. It is an object of the present invention to use computer modeling to ensure that prosthesis components are placed in such a way that the mechanical axis of the leg is not located far behind the knee center (330b) when in full-extension, as this would cause overexertion (340b) of the quadriceps muscle while the patient is standing. Individual patient functional characterization and computer simulation prior to surgery can help prevent this situation.

Figure 3:
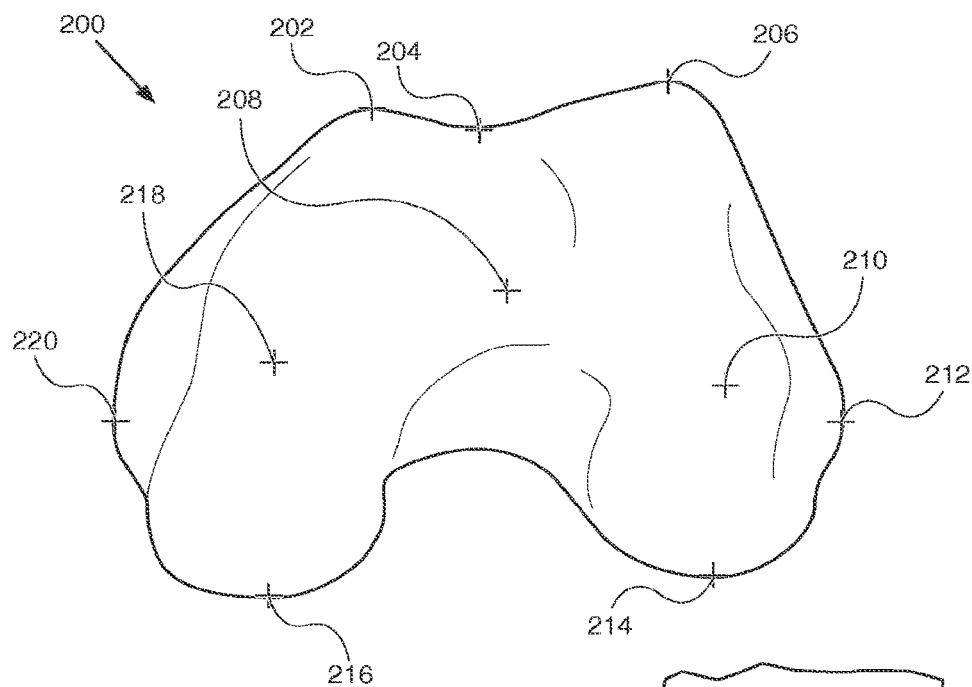
FIGS. 3-5 are distal, anterior, and posterior views of a distal femur, respectively, showing some anatomical landmarks that may be extracted from conventional bone scans according to some embodiments.
Figure 4:
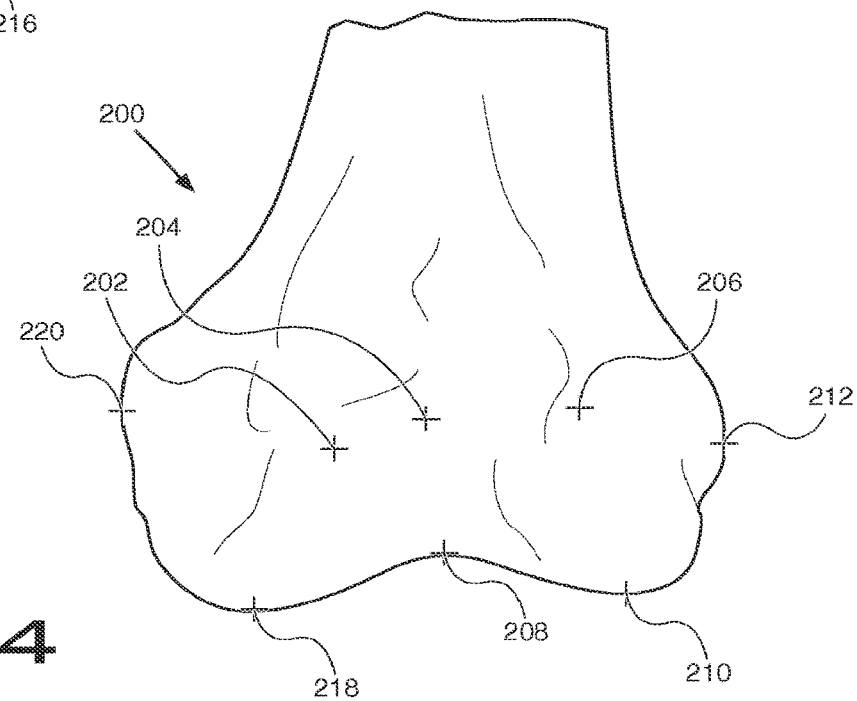
Figure 5:
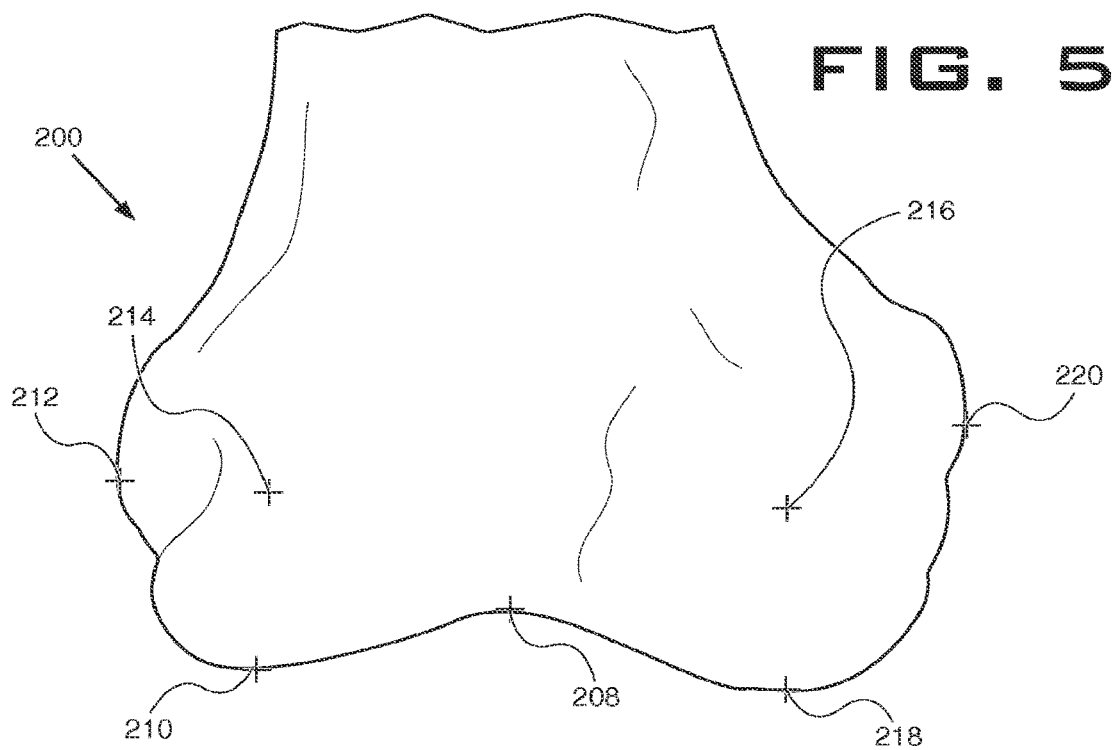

FIGS. 3-5 are distal, anterior, and posterior views of an individual patient's distal femur (200), respectively, each showing preferred anatomical landmarks (202, 204, 206, 208, 210, 212, 214, 216, 218, 220) which can be extracted from conventional scanning techniques. The conventional scanning techniques used to extract anatomical landmarks may comprise, for instance, CT scans, MR scans, radiological scans, ultrasound scans, X-rays, or the like. FIGS. 8a-8d illustrate a hip center (244) anatomical landmark, which is not visible in FIGS. 3-5. The anatomical landmarks shown in the figures are preferably used with computer modeling and simulation methods disclosed herein. Anatomical landmarks may include, but are not limited to: femoral head center (244), most distal trochlear sulcus point (208), medial epicondyle sulcus point (220), lateral epicondyle point (212), most anterior medial point (202), most anterior trochlear sulcus point (204), most anterior lateral point (206), most distal medial point (218), most distal lateral point (210), most posterior medial point (216), and most posterior lateral point (214). Once anatomical landmarks are extracted, various dimensions (222, 224, 226, 228, 230, 232, 234, 236, 238, 240, 242) may also be determined in order to characterize a patient for both anatomic and biomechanic alignment. It should be understood that while FIGS. 3-8e only show anatomical landmarks and methods of determining the same for a distal femur, one of ordinary skill in the art could readily apply the same methods to determine anatomical landmarks and various dimensions for any one of a tibia, a fibula, a humerus, an ilium, a radius, an ulna, or another bone. Anatomical landmarks may also include soft tissue attachment points.

Figure 6:
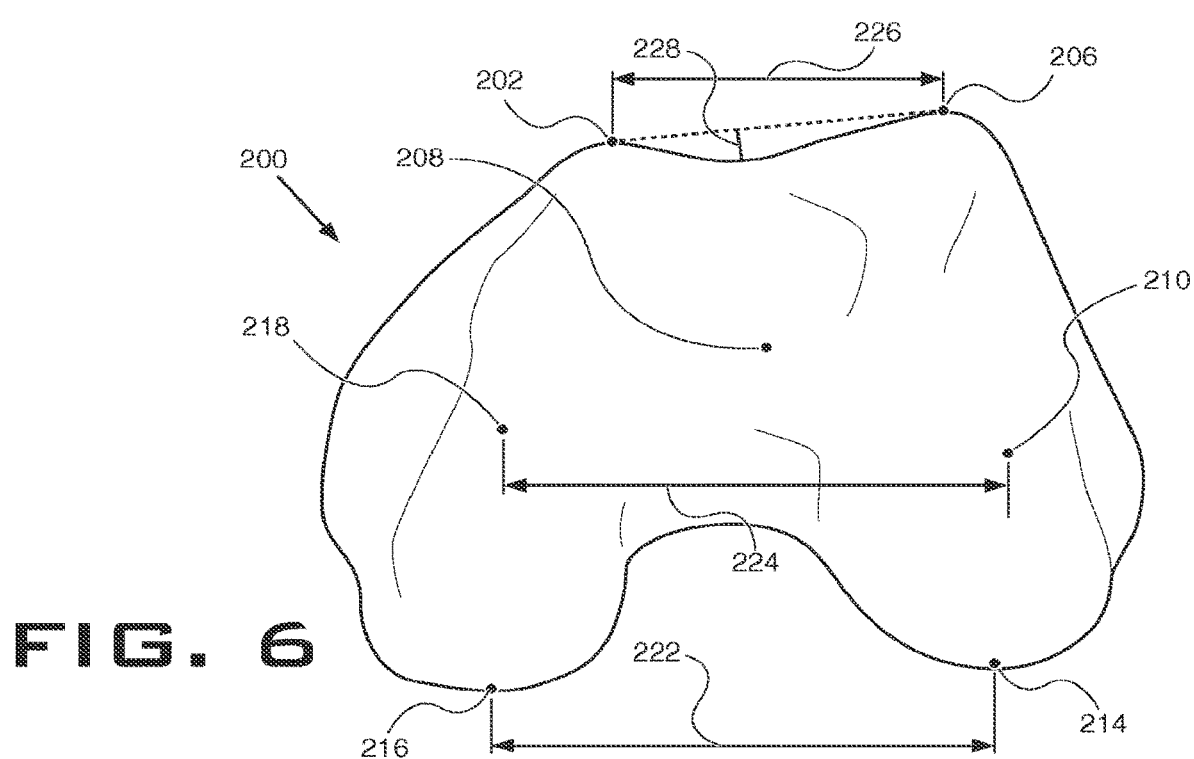
FIG. 6 is a distal view of a distal femur showing measurements taken from the extracted anatomical landmarks shown in FIGS. 3-5, and which may be used in computer simulation models according to some embodiments.
Figure 7:
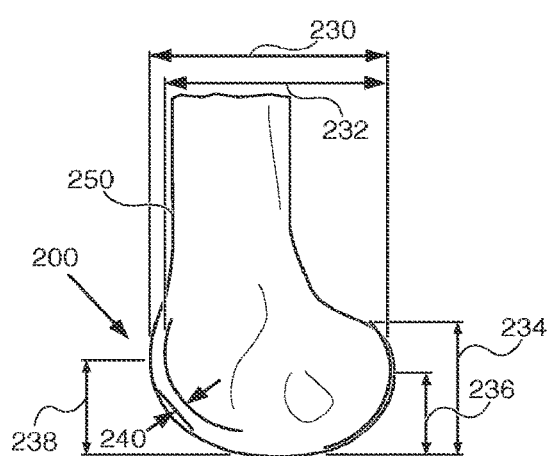
FIG. 7 is a sagittal view of a distal femur showing measurements taken from the extracted anatomical landmarks shown in FIGS. 3-5 and used in computer simulation models according to some embodiments.

FIGS. 6 and 7 illustrate some of said various dimensions (222, 224, 226, 228, 230, 232, 234, 236, 238, 240, 242) that may be extracted from the anatomical landmarks (202, 204, 206, 208, 210, 212, 214, 216, 218, 220). For example, a distance (222) between the most distal lateral point (210) and the most posterior medial point (216), a distance (224) between the most distal medial point (218) and the most distal lateral point (210), a distance (226) between the most anterior medial point (202) and the most anterior lateral point (206), and a trochlear groove depth (228) measured perpendicular to a line connecting the most anterior medial point (202) and the most anterior lateral point (206) can all be measured for different patients and stored in one or more databases. Moreover, a distance (236) between one or both of the most distal points (210, 218) and one or both of the most posterior points (214, 216), a distance (234) between one or both of the most distal points (210, 218) and one or both of the superior ends of medial and lateral condyles, a distance (238) between one or both of the most distal points (210, 218) and one or both of the points (202, 204, 206), a distance (230) between one or more most anterior points (202, 206) and one or more most posterior points (214, 216), and a distance (232) between one or more cortex or sulcus points (204, 250) and one or more most posterior points (214, 216) may be measured for different patients and stored in said one or more databases.

Each database described herein may include any one or more of an image dataset, an imageless dataset, an equation, a tolerance, a geometric model, patient anatomical data, or a parameter relative to the anatomy. Databases may further comprise biomechanic function characterization data, anatomical landmark data (e.g., soft tissue attachment points), and data relating to various relative dimensions between anatomical landmarks. The databases may be used to develop one or more patient characterization charts or lookup tables by running hundreds of implant simulations to see which implant configurations provide the best results and most acceptable implant and soft tissue stresses for different generalized patient groups. Computer modeling software may reference the characterization charts, lookup tables, or databases in order to quickly determine which implant configurations to start with for a particular patient. For example, a patient is first assessed and characterized, and is then compared to a characterization chart compiled from data acquired by many cases. The characterization chart indicates which implant type(s), size(s), and relative spatial orientation configuration(s) are proven to work best for the characterization belonging to the particular patient. The implant may be installed based solely on the characterization chart, or the characterization chart may serve as a starting point for further computer simulations of the patient to fine-tune the size(s) and position(s) of one or more implant components.

Computer simulations of the patient may comprise body or knee, simulations during one or more activities. Simulations may be facilitated by software such as LifeMOD™/KneeSIM and BodySIM from LifeModeler®, Inc. San Clemente, Calif. Implant sizes, geometries, and configurations are iteratively changed between simulations to obtain the best biomechanic performance (806) from a given prosthesis design. Prosthesis designs may also be iteratively changed between simulations if a surgeon does not have a preferred brand, or if biomechanic performance circles (806, 806', 806", 806''') for a given prosthesis and patient combination are too small or mutually exclusive to provide good anatomic fit. Good biomechanic fit will help lead to a more natural feeling to the patient, and may help minimize shear forces at implant-bone interfaces.

Patient characterization and computer simulation may use anatomical landmarks of a patient alone or in combination with the aforementioned biomechanic function measurements. If both anatomic measurements (i.e. taken from bone models) and biomechanic measurements (i.e., taken from gait lab) are made, then both postoperative kinematic function (806) and bone fit performance (802) for a given prosthesis can be optimized to provide an increased overall performance value (818) to the patient.

Figure 9:
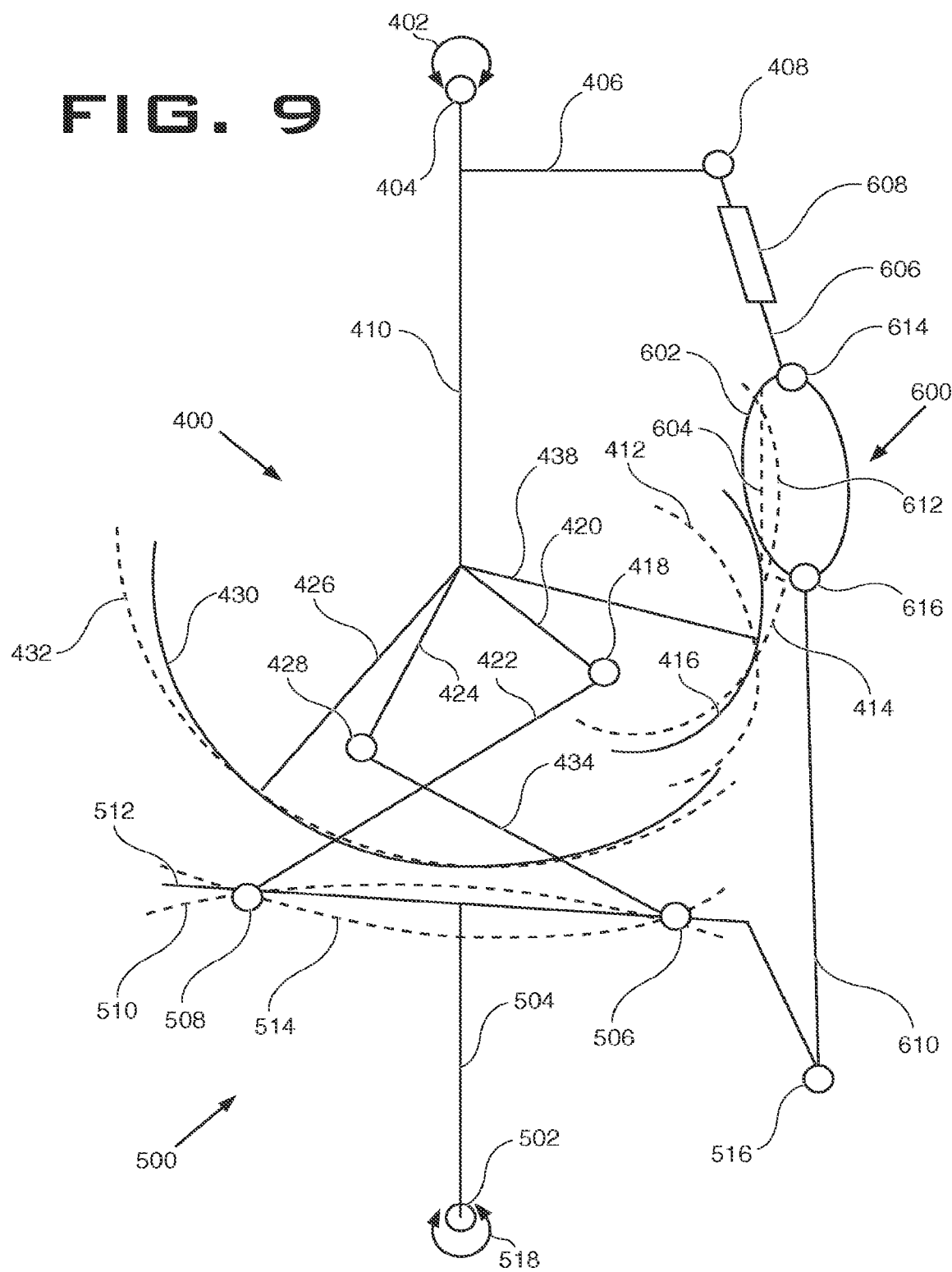
FIG. 9 illustrates a simple 2D knee model which may serve as a base model for computer simulation models described hereinafter according to some embodiments.

The anatomical landmarks (202, 204, 206, 208, 210, 212, 214, 216, 218, 220, 244) and dimensions (222, 224, 226, 228, 230, 232, 234, 236, 238, 240, 242) described herein may serve to define input parameters and input dimensions for a simulation model (400) such as the one shown in FIG. 9. For example, anatomical landmarks (202, 204, 206, 208, 210, 212, 214, 216, 218, 220, 244) and dimensions (222, 224, 226, 228, 230, 232, 234, 236, 238, 240, 242) may help define the length of link (438), the length of link (410), and the location of node (404) relative to surface (416) for a particular patient, in order to customize the model (400) for said patient.

If MR scans are used instead of CT scans, additional anatomical landmarks may be extracted and defined in space relative to anatomical landmarks (202, 204, 206, 208, 210, 212, 214, 216, 218, 220, 244) and dimensions (222, 224, 226, 228, 230, 232, 234, 236, 238, 240, 242). Said additional anatomical landmarks may include, for example and without limitation, the centroids of the patient's soft tissue attachment points (408, 418, 428, 506, 508, 516, 614, 616). If the centroids of a patient's soft tissue attachment points are known and entered into a computer simulation model prior to surgery, a surgeon can intraoperatively register the patient's joint with the computer simulation model using a "biomechanic" or "kinetic" stylus (e.g., a CAS system). The surgeon finds the same centroids used in the simulations by probing around the soft tissue attachment points during the registration step in surgery. The stylus then registers with the model and communicates with the computer simulation software directly or indirectly to assist and guide the surgeon in making resections that will orient one or more of the prosthesis components for best performance characteristics as determined by the simulations. For example, expected optimum prosthesis component orientations determined by the simulation model may be downloaded into the CAS system or into intermediate software which will enable real-time comparisons between an actual prosthesis component placement as measured with the stylus and a desirable prosthesis component placement. The stylus may provide instant feedback to a surgeon throughout surgery, such as information regarding an expected performance characteristic of the prosthesis for the instant prosthesis configuration and orientation, or a recommendation on how to re-configure, re-size, and/or re-orient the prosthesis components in order to increase one or more of the performance characteristics mentioned throughout the specification. In general, a greater amount of information inputted into the computer simulation models and a greater number of simulation iterations of prosthesis size and orientation will result in better placement recommendations for one or more prosthetic devices for a particular patient.

Figure 8A:
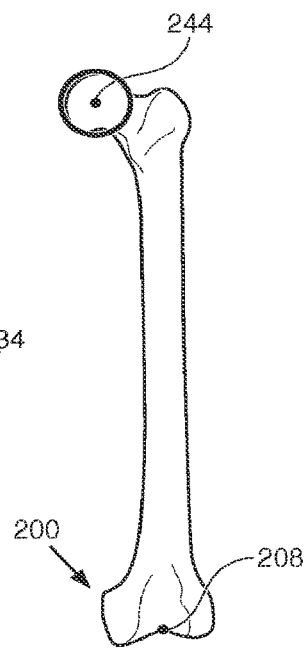
FIGS. 8a-8c are frontal views of a femur which illustrate steps for identifying and extracting the anatomical landmarks shown in FIGS. 3-5 according to some embodiments.
Figure 8B:
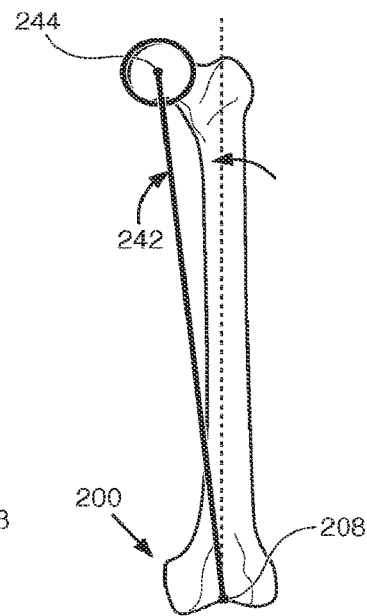
Figure 8C:
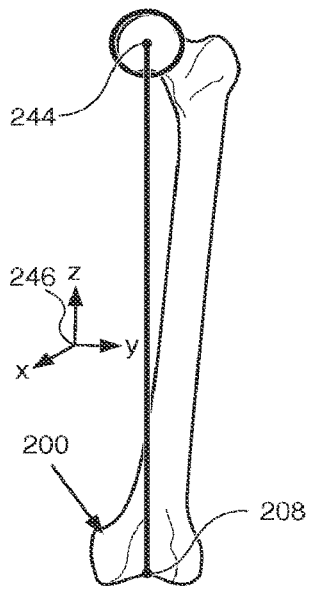
Figure 8D:
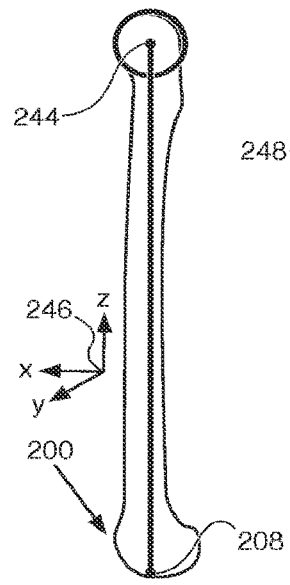
FIG. 8d is a sagittal view of a femur which illustrates a step for identifying and extracting the anatomical landmarks shown in FIGS. 3-5 according to some embodiments.
Figure 8E:
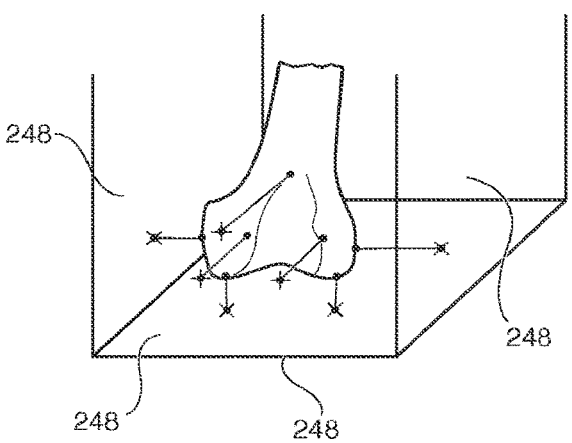
FIG. 8e is an isometric view graphically illustrating how computer assisted design (CAD) software tools may be used to automatically identify and extract anatomical landmarks according to some embodiments.

FIGS. 8a-e illustrate one embodiment of how anatomical landmarks can be extracted from anatomical scans. First, CT or MRI scans (e.g., DICOM format files) are imported into a modeling software (e.g., MIMICS by Materialise) in order to create one or more bone models of a particular patient or patient population. Since bone models can have different relative spatial orientations after digital processing, they are re-oriented and/or scaled by at least one dimension (242) so that they are aligned in all axes and sized with respect to a standard reference frame and scale (246) and scale as shown in FIGS. 8c and 8d. For example, the mechanical axis of a femur may be aligned with a Z-axis of the standard reference frame and scale (246), and the A-P Leo Whiteside's line may be aligned with an X-axis of the standard reference frame and scale (246). Alternatively, the mechanical axis of a femur may be aligned with a Z-axis of the standard reference frame and scale (246), and the epicondylar axis may be aligned with a Y-axis of the standard reference frame and scale (246). The bone models may go through segmentation filters and pre-processing steps at any point in the process to create a highly accurate model. The bone models may contain other biological features such as articular cartilage and soft tissues.

Each model is imported into a CAD software package (e.g. Unigraphics/NX, CATIA, AutoCAD, Pro/Engineer, SolidWorks, etc.) from the modeling software (e.g., MIMICS). The abovementioned step of re-orienting and/or re-scaling the bone models so that they are aligned with a standard reference frame and scale (246) may be done in said CAD software package. In the CAD software, the bone model may be placed within art arbitrary box having planar walls (248). A simple shortest distance CAD function can be used to automatically detect the shortest or longest perpendicular distances between the walls (248) and the bone model. The shortest perpendicular distances will generally yield the most anterior, most distal, and most posterior points, whereas the longest perpendicular distances will generally yield the deepest sulcus points.

In total knee arthroplasty (TKA), a surgeon may determine the size of a femoral knee implant component by measuring the A-P width (230) of the distal femur from an anterior coronal plane to a posterior coronal plane. Bone sizing is done to determine the closest size femoral component without notching the anterior femoral cortex (250). Due to noticeable gaps in A-P width (230) between sizes of femoral components within a particular orthopedic product portfolio, the biomechanic fit, feel, and function of the implant is compromised in three different ways for three different techniques, respectively.

First, if a surgeon decides to use a posterior referencing technique (i.e., referencing from anatomical landmarks 214 and 216), the anterior flange of the femoral component implant will fall where it may depending on the anterior-posterior size of the implant. In many cases, a patient's bone size falls between the sizes dictated by an orthopaedic product offering. White providing better bone coverage, using a larger sized implant with a posterior referencing technique can lead to patella stuffing, retinacular stretch, patello-femoral ligament stretch, quadriceps and patellar tendon over-stretching, quad inefficiency, and anterior knee pain due to increased forces on the patella. Conversely, using a smaller sized implant with a posterior referencing technique might cause loose quadriceps and patellar tendons, patellar subluxation, poor patellar tracking, and knee joint instability/laxity.

Second, if a surgeon decides to use an anterior referencing technique (i.e., referencing from anatomical landmarks 202 and 206), one or more posterior condyles of the femoral component(s) will fall where they may depending on their sizes and geometries. In many cases, a patient's bone size falls between the sizes dictated by an orthopaedic product offering. While providing better bone coverage, using a larger sized implant with an anterior referencing technique can lead to increased collateral ligament tension, a tight-joint in flexion, decreased range of motion, and increased risk of injury to soft tissues such as the ACL and PCL. Conversely, using a smaller sized implant with an anterior referencing technique might cause joint laxity in deep flexion, loose collateral ligaments, and pseudo-patellar baja if a thicker tibial insert is used to compensate for the laxity in flexion.

Third, while it is uncommon to do so, if a surgeon decides to take a middle-of-the-road technique (i.e., arbitrarily referencing somewhere between anterior referencing and posterior referencing), there may be a combination of the aforementioned disadvantages, or them may be a more ideal implant position (e.g., performance value 814; than what is chosen (e.g., performance value 812) based purely upon anatomic fit (802) and non-kinetic intra-operative ligament balance (804).

Another cause of unnatural feeling for patients undergoing TKA is the inherent differences between the natural articulation surface geometries of the anatomy of the patient, and the pre-defined articulating surface geometries of the chosen prosthetic implant. For example, even if a properly-sized prosthetic implant is installed in a position which best approximates the patient's existing anatomy, there will be inherent geometric differences (240) between where the artificial articulation surfaces lay with respect to the previously existing natural articulation surfaces of the patient, unless the implant is custom made. The extent of these geometrical differences (240) will determine how close the biomechanics of the replaced joint will match the natural biomechanics of the patient prior to surgery.

The above methods of "best-fitting" an implant to a bone for best bony coverage may not create the most natural feeling possible for a patient, because such methods only take into consideration anatomic fit (802) and non- or low-kinetic intra-operative ligament balance performance (804). Such methods do not simultaneously address or consider expected biomechanic performance (806) during various postoperative activities as does the present invention.

In order to improve biomechanic performance (806), it is an object of the present invention to provide a means for determining the best biomechanic sizing of components for a given prosthesis and patient. Biomechanic sizing (i.e., kinetic sizing) may be defined as a step of determining an optimum implant component size, such that when said implant component is installed in an optimum orientation and configuration suggested by simulation model results, it will provide the most natural and optimum force environments, range of motion, feeling, and biomechanic patterns for a particular patient. Good biomechanic sizing may require slight overhang of an implant, or slightly less bony coverage than would typically be desirable according to conventional methods, but will potentially increase the probability of patient satisfaction during post-operative activities. For example, a small tri-compartmental femoral component positioned in a first orientation on an individual patient which results in less bone coverage may provide higher functional biomechanic performance values than a larger tri-compartmental femoral component positioned in a second orientation that provides better bone coverage. In this instance, the small tri-compartmental femoral component would be considered to be better biomechanic oily-sized than the larger tri-compartmental femoral component.

In all instances, a surgeon would have the opportunity to make compromises as he or she sees fit, through the use of modular implants or a larger implant selection. A surgeon may, at any time, abandon the recommendations generated from the computer simulations of the invention. The invention primarily serves to give a surgeon more options to consider both before and during surgery. The invention does not reduce the number of options permitted.

According to some embodiments, there is provided a method of tuning the orientation of one or more prostheses prior to implantation to give the best biomechanic performance (806), somewhat regardless of bone fit as conventionally done. First, a forward dynamic computer model of virtual patient is created. Such model may be created with BodySIM software by LifeMOD™. The model is then used to "virtually" implant one or more prostheses (e.g., TKA component, uni-compartmental component, bi-compartmental component) into the patient and determine which configuration(s) and orientation(s) of said one or more prostheses will yield the best biomechanic performance, range of motion, and soft-tissue force environment throughout designated activities. Depending on a patient's lifestyle demands, an ideal implant size, type, brand, and spatial orientation(s) for each component of a prosthesis is chosen based on iterative modeling and simulating. The prosthesis components are then implanted accordingly.

The computer simulations described throughout this disclosure may comprise virtual patient computer models built from anthropometries of the patient prior to surgery using any one or more of motion capture, force plate data, stair climb data, stair descend data, chair rise data, etc. The virtual patient computer model may also be built by CT or MR data of bones such as those shown in FIGS. 3-8*d*, to allow anatomic fit (802), and biomechanic performance (806), and ligament balance (804) optimization. Once the virtual patient computer model is built, a surgeon or engineer can perform iterative virtual surgeries on the virtual patient to determine the best implant configurations for the patient's functional envelope. Iterations may be done manually or automatically through computer automation. Parameters such as femoral component size, type, brand, and spatial orientation are changed within the virtual patient model either manually or automatically for each iteration. For example, femoral joint line orientation, femoral varus/valgus orientation, femoral internal and external rotation orientation, femoral flexion/extension orientation, and other femoral spatial orientations may be iteratively changed within the model to "tune" a femoral component position for optimum results. Additionally, several parameters such as tibial component size, type, brand, and spatial orientation can be changed within the virtual patient model. For example, tibial internal and external rotation, tibial posterior slope, tibial A-P positioning, tibial varus/valgus orientation, as well as other tibial spatial orientations may be altered to "tune" a tibial component implant either alone or in combination with the abovementioned femoral component. Moreover, several parameters such as patellar component size, type, brand, and spatial orientation relative to the femoral component and/or tibial component can be changed within the virtual model to obtain a total configuration that yields the best implant performance characteristics for the particular patient's anatomy, biomechanic function, and lifestyle.

In some instances, the placement of the patella component implant on patellar bone may be moved superiorly, inferiorly, laterally, medially, or combinations thereof, according to the most favorable results of the virtual patient computer model, in order to "tune" the patellar component implant position for best performance, optimum tracking, lowest soft tissue stresses, lowest patellar tendon stresses, lowest quadriceps forces, optimum Q-angle, optimum collateral ligament tension, optimum retinaculum tension, lowest patellar shear stresses, lowest cement interface shear stresses, and/or lowest wear. Alternatively, the articular geometry of the patella component implant may be changed between concave (612), convex (602; and flat (604) according to the virtual patient computer model results in order to optimize the above patella performance characteristics and overall prosthesis biomechanic function. Even more alternatively, the biomechanic sizing of said patella component implant may be adjusted within the virtual patient computer model to effectively "tune" the patellar size for a particular patient.

According to some embodiments, a surgeon may set up iterative virtual surgeries. After characterizing a patient's biomechanic function and/or anatomy using the methods described herein, the surgeon may virtually place one or more virtual implants on an individual patient's bone model for best bony coverage and mechanical alignment as he or she would conventionally do, only using simulation software. Then, the surgeon may define one or more ranges, thresholds, variables, limits, or parameters to set a size and spatial orientation envelope for the one or more virtual implants which represent the one or more implants to be implanted into the patient. For instance, an envelope for said one or more virtual implants may be defined by input received from surgeon or engineer prompts. Prompts may include, for example, maximum or minimum limits for implant size, changes in position (mm) in a medial-lateral direction, changes in position (mm) in an inferior-superior direction, changes in angular position (degrees; of internal/external rotation, changes in angular position (degrees) of varus/valgus, changes in angular position (degrees) of flexion/extension, and changes in position (mm; in an anterior-posterior direction. Computer simulations will then be run, with each iteration slightly modifying the position of the one or more implants within the defined envelope.

For example, a surgeon or engineer may first virtually size and virtually implant a virtual femoral component and a virtual tibial component into a virtual patient model for best bone fit and mechanical axis alignment as would conventionally be done; however, using software instead of an actual trial reduction step during surgery. This initial virtual sizing and virtual placement would be based on common techniques such as using epicondylar axis and Leo Whiteside's line to determine internal and external rotation, and may be considered a crude start for optimizing biomechanic performance (806). The surgeon then requires that a maximum and/or minimum of N computer modeling simulation iterations (wherein, N is a specified number of iterative virtual surgeries) are used to virtually position the virtual femoral component differently within a spatial orientation envelope of ±2 mm in a medial-lateral direction, ±2 degrees of internal/external rotation, ±2 degrees of varus/valgus, and ±2 mm in an anterior-posterior direction, and a predetermined spatial orientation resolution of 0.1 mm and 0.1 degrees (i.e., the amount to change each input variable between simulation iterations).

After the virtual surgery simulations are finished and the data is compiled, one or more suggested sizes and/or relative spatial orientations of the virtual femoral component and virtual tibial component are displayed, along with one or more expected performance characteristics [e.g., expected metallic or polymeric volumetric wear rate, ligament tension (e.g., MCL, LCL, ACL if applicable, and PCL if applicable), range of motion, efficiency, stress environment(s), biomechanic environment(s), fixation strength, ligament balance, anatomic fit (e.g., bone fit), fixation force(s), implant longevity, tibiofemoral and patellofemoral kinematics throughout a range of motion (e.g., maximum flexion, maximum internal/external rotation, maximum patella flexion and tilt, maximum femoral rollback), quadriceps force] associated with said suggested sizes and relative spatial orientations. The surgeon may then decide to re-orient the components of the prosthesis based on expected performance characteristics calculated by the software, in order to optimize anatomic fit and biomechanic performance.

Natural feeling (e.g., proprioception) and biomechanic performance of an implant can be better established with the present invention if the implant is custom-designed or otherwise an implant specifically designed for use within a niche characterized patient population to which the patient belongs. For instance, an implant brand or type that is designed specifically for any one or more of the patient's race, build, religion (e.g., frequently used prayer stances), hobby (e.g., golf, biking, hiking), gender, activity level (high vs. low), and lifestyle may improve biomechanic performance when the novel installation tuning methods of the present invention are used.

The benefit of the present invention is that a surgeon can perform hundreds of virtual surgeries by means of iterative analysis, in order to determine the optimal size, optimal placement, optimal spatial orientation, optimal alignment, and/or the best performance compromise between anatomic fit (802) and biomechanic function (806), all while taking into consideration intra-operative soft tissue constraints such as ligament balance (804). Optimization parameters may include, but are not limited to: minimizing bone-implant interface stresses, reducing stress-shielding and/or implant subsidence, minimizing quadriceps and hamstring co-contraction, minimizing quadriceps forces required for various activities, achieving a natural screw-home position as shown in FIG. 2a, reducing stress on posterior knee tissues, reducing shear loads and stresses on the patella-bone interface, matching EMG patterns or individuals with normal joint function and normal biomechanic function, achieving normal kinematics, and achieving proper ligament tension and constraint for one or more of the ACL, PCL, MCL, and LCL.

Computational models described herein are preferably driven by kinematics from motion capture, and then subsequently driven by forward dynamics from virtual muscles in a similar manner as the LifeMOD™ body simulating models described above.

The methods provided by the present invention may be advantageously used as preoperative planning tools for determining optimal alignment and positioning of all types of prosthetic components and may even be used to construct patient-specific cutting guides and instruments (e.g., saw blade cutting blocks, drill guide blocks, router guide blocks, and mill guide blocks). In other words, after iteratively running a body simulation of a patient's knee (or other joint) with slightly different sizes and/or spatial orientations of a particular orthopedic implant during each iteration, and after determining which spatial orientation(s) and/or sizes of said orthopedic implant provides the best overall prosthesis performance value (814), one or more patient-specific cutting guide devices may be produced from the modeling software and/or patient scans. The patient-specific cutting guide devices may be rapid-manufactured (e.g., via selective laser sintering (SLS)) and generally serve to guide a surgeon's resections, cuts, and holes in order to position the implant on the patient in the same spatial orientation which provides said best overall prosthesis performance value (814). The patient-specific cutting guide devices described herein may comprise cutting blocks which preferably have at least one B-spline 3D surface portion, or at least three strategically positioned contact points that conform to a bony or cartilaginous articulating or non-articulating surface of the individual patient's joint. The B-spline 3D surface portion or the at least three strategically positioned contact points spatially orient the block in all six degrees of freedom relative to the patient's bony anatomy in such a way that the bony resections facilitated by said patient-specific cutting guide devices will effectively position one or more implants in the same optimal spatial orientation (relative to said patient's bony anatomy) suggested by the modeling software.

The virtual patient testbed described herein may be used, in much the same manner as the KneeSIM Oxford rig model is conventionally used to design implant geometries. Many simulations can be run in a validated model to customize and optimize the spatial orientation(s) of a designated implant for a particular patient. Optimization is achieved by iteratively varying many different input variables and parameters in the model, running the model, recording the results, compiling the results after a predetermined number of model iterations is completed, processing the results, comparing the results, and then selecting the result or results that provide desired or acceptable overall performance. Once models are validated for different patient activities (e.g., climbing, biking, hiking, golf, walking, kneeling, etc.), they may be re-used for different patients by simply changing input parameters based on a patient's anthropometric functional characterization (116) and/or anatomic blueprint.

FIG. 9 illustrates a two-dimensional kinematic/kinetic knee simulation model according to some embodiments of the present invention. The model shown may be loaded into a computer program to optimize one or more performance characteristics of one or more knee prosthetic components implanted into an individual patient's affected joint. The model may be as simple or as complex as is necessary to optimize a performance characteristic of a prosthetic device, and is not in any way limited to what is shown in FIG. 9. For example, similar models may be similarly created for hip, shoulder, ankle, and/or extremity applications. More complex three-dimensional models (as shown in FIGS. 14a-c) may also be created using computer software (e.g., KneeSIM and BodySIM by LifeMOD™). With advancements in simulation programs, one of ordinary skill can create models to very accurately simulate a patient's preoperative and post-operative biomechanic profile using the method steps provided.

The model includes a femur (400), a patella (600), and a tibia (500). Femur (400) is represented in the model as a femoral link (410), which is rotatably attached to a hip socket node (404). Femoral link (410) may pivot, about the hip socket node (404) within a range of motion (402). Range of motion (402) may be an input variable or a result outputted after simulations are run. At some distal and radial (406) distance from the hip socket node (404) (radial distance 406 representing femoral bone radius or quadriceps thickness) a link representing the quadriceps (606) is attached to the femur (400) at attachment point (408). Quadriceps (606) is pivotally attached at a superior patellar attachment point (614) and may comprise an actuator or a spring damper (608) function to simulate contraction and damping during muscle firing. The inferior portion of patella (600) is pivotally connected to a patellar tendon (610) at node (616). Patellar tendon (610) is pivotally connected to the tibia (500) at a node (516) adjacent or on the tibial tubercle (not shown). Femur (400) comprises a patello-femoral surface (416) and a condylar surface (430). Femur (400) also comprises an ACL attachment point (428) and a PCL attachment point (418). The attachment points (418, 428) are connected to the femoral link (410) by rigid links (420) and (424), respectively. Similarly, condylar (430) and patello-femoral (416) surfaces are connected to the femoral link (410) by rigid links (430) and (438), respectively. Femur (400) is kinematically coupled to tibia (500) by ACL (434) and PCL (422), which are both pivotally attached thereto, ACL (434) and PCL (422) are flexible links similar to rope. Tibia (500) is represented as a tibial link (504) with medial or lateral bearing surface (512) and having an ACL attachment point (506) and a PCL attachment point (508). The tibial link (504) is adapted for an amount of rotation (518) about an ankle node (502). MCL (not shown) function and LCL (not shown) function may be represented by the model shown in FIG. 9 in much the same fashion as the ACL (434) and PCL (422) are represented.

After gathering a patient's biomechanic function data, information is inputted into the model to create a patient-characterized model. For instance, an MRI might reveal relative spatial locations of centroids of soft-tissue attachment points (408, 418, 428, 506, 508, 516, 614, 616) and lengths, thicknesses, and densities of ligaments (422, 434, 610). Force sensors in a gait lab may help determine parameters for quadriceps function modeling (608), X-ray scans may be used to determine the length of tibial (504) and femoral (410) links.

Next, several patient characterized model simulations are run, with finite changes to any one or more of implant type, brand, shape, size, and spatial orientation during each simulation. For example, if the patient's favorite hobby is gardening, the patient-characterized model simulation may include forces and moments applied to femoral link (410), tibial link (504), patella (600), and quadriceps muscle (606) which are representative of a typical kneeling pattern common during gardening. In some instances, the condylar surfaces (430) may be positioned differently, or the geometries of the condylar surfaces (430) be made less circular, less arcuate, or B-splined as shown by numeral (432). Condylar surfaces (430) may comprise a series of joined arcuate portions, each arcuate portion having a radius dimension that can be changed between simulation iterations in order to help select the best prosthesis design. During some simulation iterations, the patello-femoral surface (416) may be oriented differently in space as indicated by numerals (412) and (414). Patellar articulating surfaces may be changed from convex (602) to flat (604) or concave (612) between simulation iterations. Tibial bearing surfaces (512) may me changed in convexity (510) or concavity (514) on the medial and/or lateral sides between simulation iterations. Preferably, the relative positioning between the patellofemoral surface (416) and condylar surface (430), and the relative positioning between surfaces (416, 430) and the patient's anatomy is changed between simulations, as the inventors have found these relationships to be important factors in increasing biomechanic performance.

After simulations am run, results including one or more performance characteristics are outputted, and recommendations are made based on performance analysis. As mentioned earlier, the surgeon has the final say as to final implant brand, size, shape, and spatial orientations of the implant(s), but he/or she may take the recommendations into consideration prior to and during surgery.

During surgery, the surgeon may use a stylus which allows intraoperative measurement of biomechanic alignment and compares said intraoperative measurement and alignment with pre operatively determined optimum computer simulation results. Such a stylus may be used in conjunction with a computer assisted surgery (CAS) device. The stylus serves several purposes. First, it allows a surgeon to assess bone fit and biomechanic fit at any time during surgery by continuously registering and comparing actual trial, implant or permanent implant locations relative to bone and other trials with preoperative computer simulation results. Second, the stylus provides information that allows a surgeon to pick which alignment he favors while still being able to receive instant feedback on predicted performance for the configuration chosen. Thirdly, the stylus informs the surgeon how close the implant(s) or trial implant(s) is positioned in the patient, relative to the optimized configuration determined by the model simulations.

For example, if a patello-femoral articulating surface (416) and condylar surface (430) such as the ones shown in FIG. 9 are not part of a monolithic femoral component (that is, they are each portions of separate patellofemoral implant surfaces and medial unicondylar femoral implant surfaces, respectively), relative geometric conditions or spatial orientations between the surfaces (416, 430) may be suggested from the simulation results. One example of such a suggestion might be how to make implant surfaces (416, 430) more tangent to reduce patella skipping, patellar binding, patella baja, patellar rotation, and/or patellar shear.

During surgery, the model (400) may be used in a loop feedback CAS surgical navigation system in order to obtain instant expected performance results for a given implant configuration. This may be done by registering the patient's anatomy and one or more components of the implant. The CAS surgical navigation system may suggest one or more different relative spatial orientations between said one more components, or the CAS surgical navigation system may suggest one or more different relative spatial orientations between said one or more components and the patient's anatomy. Performance results expected from the suggested component orientations may be outputted so that a surgeon is better equipped to make intraoperative decisions.

Alternatively, while not preferred due to large runtimes, the computer simulations discussed herein may be done intraoperatively using conventional CAS surgical navigation systems. During a procedure, the surgeon probes one or more implant trials to convey real-time information to the CAS system about the relative positions between said one or more implant trials, and/or the relative positions between said one or more implant trials and a patient's anatomy. The CAS system then inputs the information into a simulation model such as the one shown in FIG. 9 during the surgical procedure, and a simulation is run. The simulation model may be run on the CAS software on an external platform. Results of the simulation are preferably instantaneously fed back to the surgeon through the CAS interface. The CAS system may provide instruction or guidance as to where to move the one or more implants for better performance (802, 804, 806). Alternatively, the CAS system may just serve as a checking tool by outputting the expected biomechanic and anatomic performance results for a particular implant trial configuration measured. If the expected biomechanic and anatomic results fall within acceptable performance levels and the surgeon is happy with the results, the one or more trial implants can be removed and one or more real implants permanently implanted.

FIGS. 10a-12b illustrate several implant trial components which may be used in combination with, or independently of the methods disclosed herein, in order to measure, quantify, and define the biomechanic function of an artificial knee joint intraoperatively.

Figure 10A:
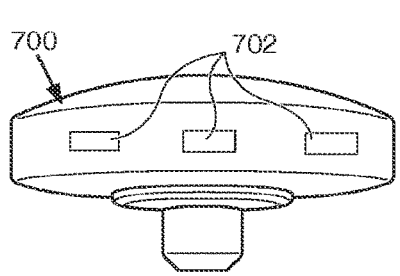
FIGS. 10a-c illustrate several different embodiments of patellar trials incorporating force transducers for intra-operative feedback and/or model input.
Figure 10B:
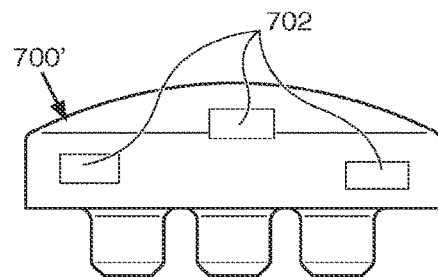
Figure 10C:
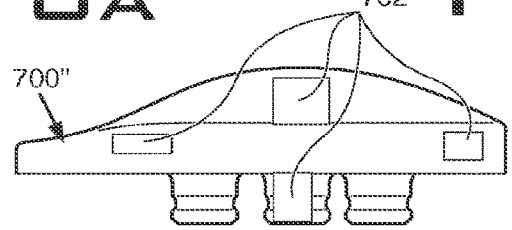

FIGS. 10a-c illustrate patellar trial buttons (700, 700', 700") that each comprise one or more force transducers (702), strain gauges (702), accelerometers (702), or one or more position markers (702). Position markers may comprise, for instance, CAS arrays, fiducial markers, and/or tantalum beads for use with radiostereometric analysis. Using Bluetooth® wireless technology, interconnected wires, serial port cables (e.g., FireWire by Apple, USB), or other means, the one or more force transducers (702), strain gauges (702), accelerometers (702), or position markers (702) communicate with a computing device (not shown) that displays force measurements during trial reduction. Magnitude and direction of forces and stresses may be measured and displayed for one or more degrees of freedom at one or more locations, or they may be fed back into the virtual model, for subsequent validation or comparison. For example, for a patella button (700, 700', 700") according to some embodiments, the side force at the cement-bone interface may be recorded and displayed, as well as the normal force experienced at the trochlear groove contact point. The computing device generally converts small electrical voltage potential changes caused by deflections in said transducers (702), strain gauges (702), and accelerometers (702) to quantifiable stresses, loads, or accelerations that can be displayed to a surgeon during trial reduction.

For example, during trial reduction, a surgeon may test patellar tracking with a patellar implant trial component (700) as shown in FIG. 10a. If at some point during knee flexion, the computing device reads unacceptably high stress values, the surgeon may switch to another patellar implant trial design (700', 700") such as the ones shown in FIGS. 10b and 10c to reduce the stresses, or the surgeon may reposition the patellar implant trial (700) or other implant trials (700', 700") to reduce the stress. Instant surgeon feedback is achieved.

Figure 11A:
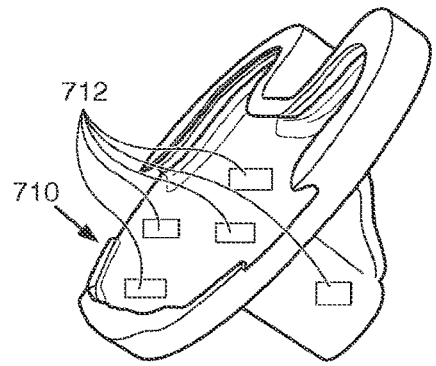
FIGS. 11a-c illustrate several different embodiments of tibial trays incorporating force transducers for intra-operative feedback and/or simulation model input.
Figure 11B:
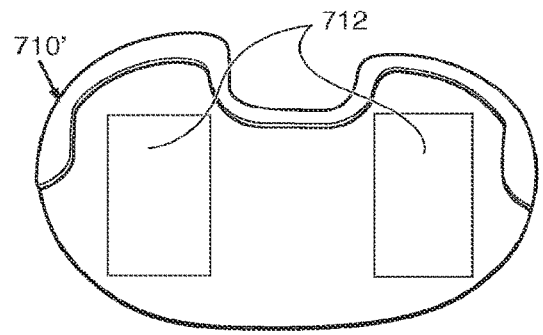
Figure 11C:
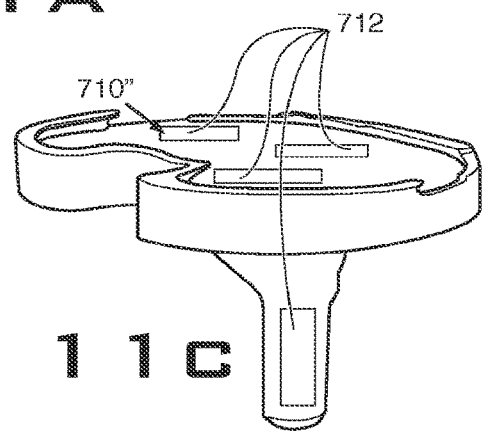

FIGS. 11a-c illustrate tibial trays (710, 710', 710") that each comprise one or more force transducers (712), strain gauges (712), accelerometers (712), or one or more position markers (712). Position markers may comprise, for instance, CAS arrays, fiducial markers, and/or tantalum beads for use with radiostereometric analysis. Using Bluetooth® wireless technology, interconnected wires, serial port cables (e.g., FireWire by Apple, USB), or other means, the one or more force transducers (712), strain gauges (712), accelerometers (712), or position markers (712) communicate with a computing device (not shown) that displays force and stress measurements during trial reduction. Magnitude and direction of forces and stresses may be measured and displayed for one or more degrees of freedom at one or more locations, or they may be fed back into the virtual model for subsequent validation or comparison. For example, for a tibial tray (710, 710', 710") according to some embodiments, the compressive forces at both the medial and lateral condylar locations may be recorded and displayed to help assess joint balancing and flexion gap throughout a range of motion. The computing device generally converts small electrical voltage potential changes caused by deflections in said transducers (712), strain gauges (712), and accelerometers (712) to quantifiable stresses, loads, and accelerations that can be displayed to a surgeon during trial reduction.

Figure 12A:
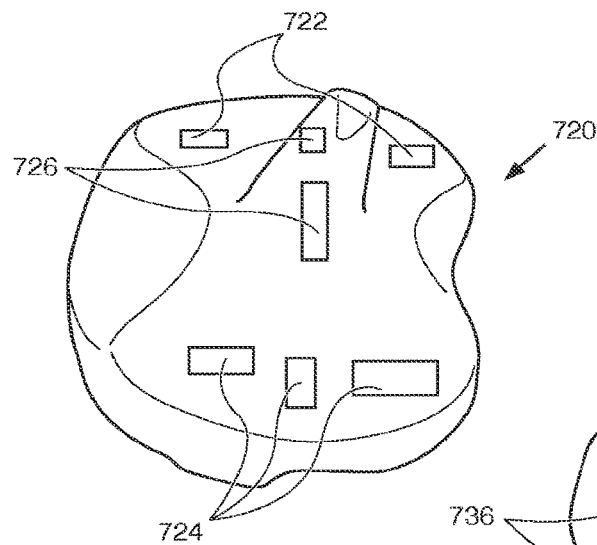
FIG. 12a illustrates a tibial trial insert incorporating one or more force transducers for intra-operative feedback and/or simulation model input according to some embodiments of the present invention.

FIG. 12a illustrates a tibial insert trial (720) that may comprise one or more medial force transducers (722), medial strain gauges (722), medial accelerometers (722), medial position markers (722), lateral force transducers (724), lateral strain gauges (724), lateral accelerometers (724), lateral position markers (724), tibial post force transducers (726), tibial post strain gauges (726), tibial post accelerometers (726), and tibial post position markers (726). Position markers may comprise, for instance, CAS arrays, fiducial markers, and/or tantalum beads for use with radiostereometric analysis. Using Bluetooth® wireless technology, interconnected wires, serial port cables (e.g., FireWire by Apple, USB), or other means, the one or more force transducers, strain gauges, accelerometers, or position markers (722, 724, 726) communicate with a computing device (not shown) that displays force and/or stress measurements during trial reduction. Magnitude and direction of forces and stresses may be measured and displayed for one or more degrees of freedom at one or more locations, or they may be fed back into the virtual model for subsequent validation or comparison. For example, for a tibial insert trial (720) according to some embodiments, the compressive forces at both the medial and lateral condylar locations may be recorded and displayed to help assess joint balancing and flexion gap throughout a range of motion. The computing device generally converts small electrical voltage potential changes caused by deflections in said transducers, strain gauges, and accelerometers to quantifiable stresses, loads, and accelerations that can be displayed to a surgeon during trial reduction. The transducers, strain gauges, accelerometers and/or position markers may be located in various areas of the tibial insert trial (720), including the tibial stabilization post to measure femoral cam impact forces applied thereto.

Figure 12B:
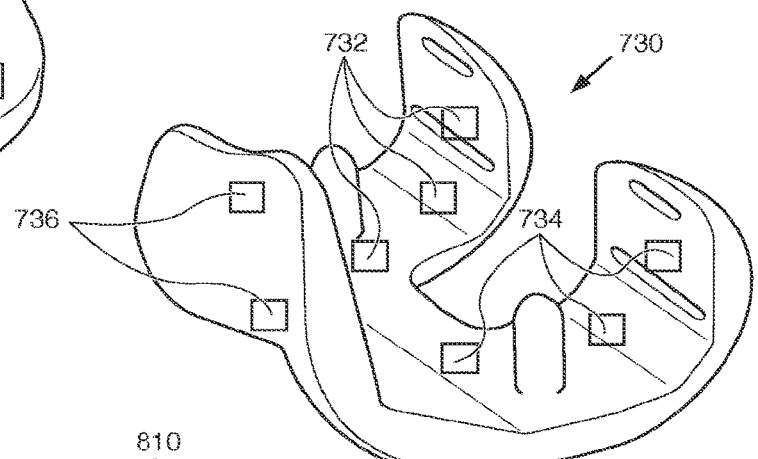
FIG. 12b illustrates a trial femoral component incorporating one or more force transducers for intra-operative feedback and/or simulation model input according to some embodiments of the present invention.
Figure 13:
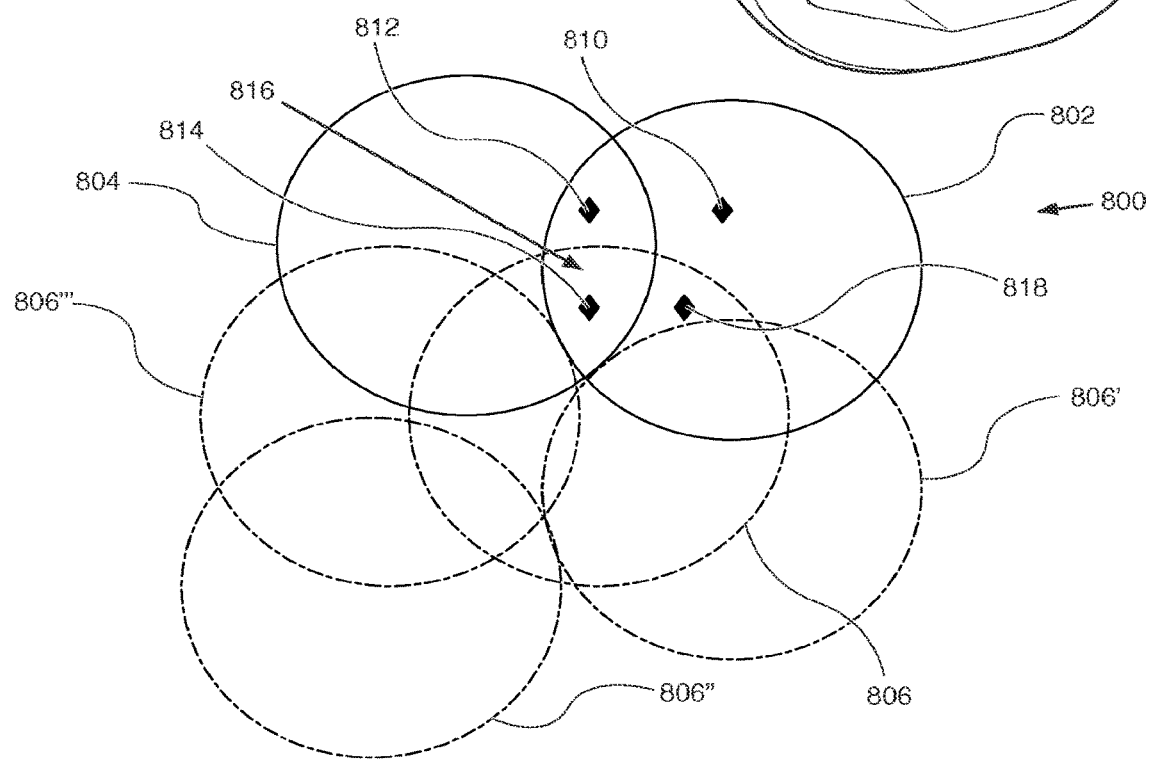
FIG. 13 is a schematic Venn diagram illustrating how the present invention aims to solve problems that currently exist in the prior art.

FIG. 12b illustrates a femoral component trial (730) that may comprise one or more medial force transducers (732), medial strain gauges (732), medial accelerometers (732), medial position markers (732), lateral force transducers (734), lateral strain gauges (734), lateral accelerometers (734), lateral position markers (734), anterior force transducers (736), anterior strain gauges (736), anterior accelerometers (736), anterior position markers (736), femoral cam force transducers (not shown), femoral cam strain gauges (not shown), femoral cam accelerometers (not shown), and femoral cam position markers (not shown). Position markers may comprise, for instance, CAS arrays, fiducial markers, and/or tantalum beads for use with radiostereometric analysis. Using Bluetooth® wireless technology, interconnected wires, serial port cables (e.g., FireWire by Apple, USB), or other means, the one or more force transducers, strain gauges, accelerometers, or position markers (732, 734, 736) communicate with a computing device (not shown) that displays force and/or stress measurements during trial reduction. Magnitude and direction of forces and stresses may be measured and displayed for one or more degrees of freedom at one or more locations, or they may be fed back into the virtual model for subsequent validation or comparison. For example, for a femoral component trial (730) according to some embodiments, the compressive forces at both the medial and lateral condylar locations may be recorded and displayed to help assess joint balancing and flexion gap throughout a range of motion. The computing device generally converts small electrical voltage potential changes caused by deflections in said transducers, strain gauges, and accelerometers to quantifiable stresses, loads, and accelerations that can be displayed to a surgeon during trial reduction. The transducers, strain gauges, accelerometers and/or position markers may be located in various areas of the femoral component trial (730), including anterior or posterior cams to measure tibial post impact forces applied thereto.

Figure 15A:
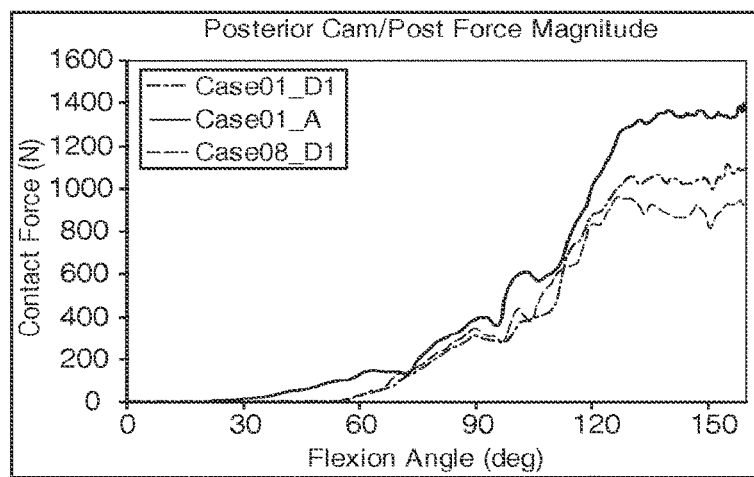
FIGS. 15a-c illustrate one method of presenting optimum predicted kinetic performance or computer simulation results for different simulation iterations.
Figure 15B:
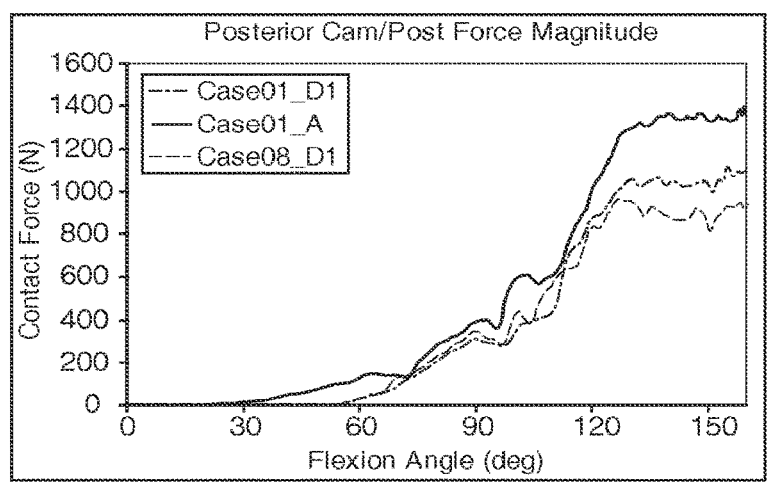
Figure 15C:
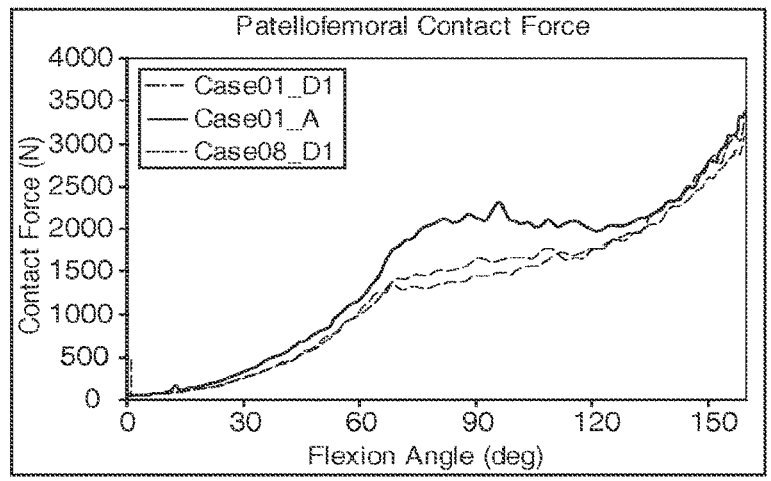
Figure 15D:
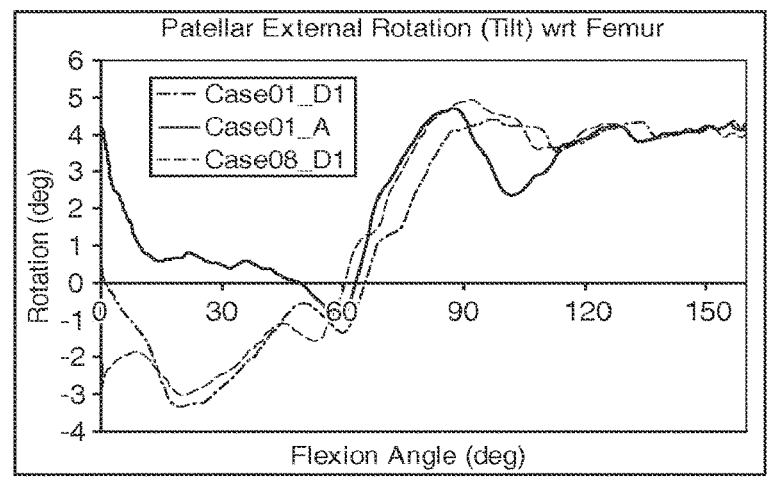
FIGS. 15d-f illustrate one method of presenting optimum predicted kinematic performance or computer simulation results for different simulation iterations.
Figure 15E:
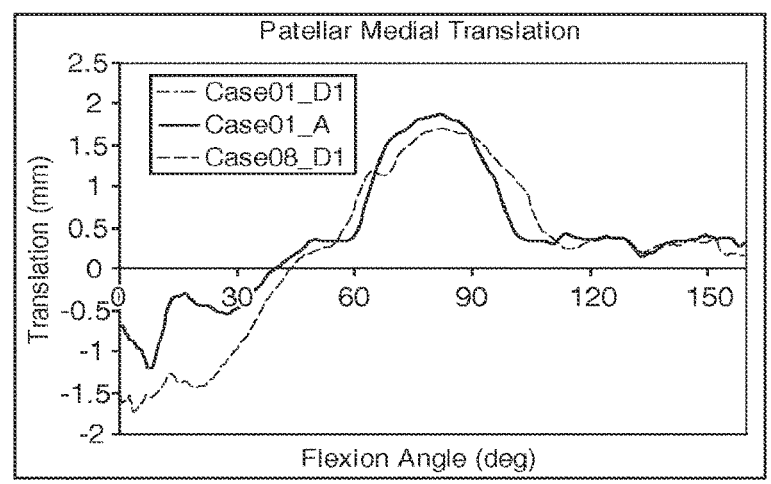
Figure 15F:
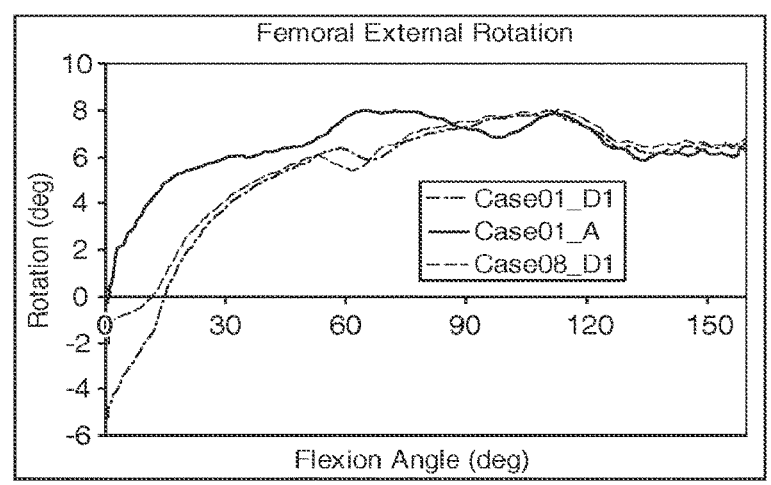

FIGS. 14a-c. illustrate 3D computer simulation models according to some embodiments of the present invention. FIG. 14a illustrates a chair rise model (900) created after patient characterization steps (110, 112, 114, 116, 118). Implants, such as a lateral unicondylar femoral implant (902) and a lateral unicondylar tibial implant (904) are virtually implanted into the model (900) by means of a detailed submodel (906). The model (900) is run for 1-N simulation iterations (where N may be any integer), during which time, the relative sizes, geometric relationships, and relative spatial orientations are changed within a predefined parameter range. The model (900) records kinetic (e.g., as shown in FIGS. 15a-c) and kinematic (e.g., as shown in FIGS. 15d-f) results for each simulation iteration and compares the results to determine the optimal relative sizes, geometric relationships, and relative spatial orientations for the implants (902, 904) to be installed in the patient. For example, expected quadriceps force (908) or Q-angle may be determined. A surgeon may use the results preoperatively or postoperatively to optimize biomechanic and anatomic fit.

FIG. 14b illustrates a patient-specific computer simulation model (910) similar to the one shown in FIG. 14a, but modified to characterize a patient's biomechanic function during a golf swing. The golf model (910) may be a preferred model to use for patients who want to enjoy playing golf without pain after prosthesis implantation. Model (910) may comprise a submodel (920) of a patient's affected joint. As shown in FIGS. 14b and 14c, submodel (920) may be, for instance, a computer simulation model of a patient's knee, comprising a total knee femoral component (916), tibial component(s) (914), and patellar component (912). It should be understood that other joints may be modeled in a submodel (920). The submodel (920) may be defined and parameterized based on anatomical landmarks and dimensions gathered from the patient using anatomical scans as shown in FIGS. 3-8e (e.g., full MRI scans), and/or the submodel (920) may be defined and parameterized based on biomechanic measurement data of the patient recorded in a gait lab.

The model (910) is run for 1-N simulation iterations (where N may be any integer), during which time, the relative sizes, geometric relationships, and relative spatial orientations of each implant component (912, 914, 916) are changed within a predefined parameter range. The model (910) records kinetic (e.g., as shown in FIGS. 15a-e) and kinematic (e.g., as shown in FIGS. 15d-f) results for each simulation iteration and compares the results to determine the optimal relative sizes, geometric relationships, and relative spatial orientations for the implants to be installed in the patient. A surgeon may use the results for preoperative planning or for intraoperative guidance to optimize biomechanic performance (806), ligament balance (804), and anatomic fit (802).

During each simulation of model (910), at least one input variable for the submodel (920) changes. For instance, a first spatial orientation (922) of femoral component (916) may be altered between iterations. Moreover, in some instances, a second spatial orientation (924) of the tibial component (934) may be altered between iterations. In yet another instances, a third spatial orientation of the patellar component (912) may be altered between iterations. Anatomical landmarks such as centroids of soft tissue attachment points may be used to define the model (910) and submodel (920). For instance, an MRI scan may allow a surgeon or engineer to define centroids of patella tendon attachment points (940, 950), quadriceps attachment points (928), medial collateral ligament attachment points (930, 934), lateral collateral ligament attachment points (942, 946), anterior cruciate ligament attachment points (not shown), retinaculum attachment points (not shown), and posterior cruciate ligament attachment points (not shown) among others. In an other instance, an X-ray or CT scan may help determine orientation, size, and geometry of a patient's femur (938), tibia (936), and fibula (952) to create the patient-specific models (900, 910, 920).

FIGS. 15a-c illustrate one method of presenting optimum predicted kinetic performance or presenting kinetic computer simulation results for different simulation iterations. While the information shown in FIGS. 15a-c is presented in the form of one or more charts, the information may be presented in other forms such as one or more tables, graphs, flowcharts, spreadsheets, data arrays, data lists, or exported data files for use with statistical analysis software. Each chart may include information concerning one or more optimum implant placements based on kinetic analysis or one or more expected performance characteristics, values, or results corresponding to said one or more optimum implant placements. Alternatively, the charts may simply show the expected kinetic performance for each geometric configuration/relationship for each iteration during an iterative computer simulation. By comparing the simulation iteration results side by side, a kinetically optimum geometric configuration/relationship between implants and/or the patient's anatomy can be selected.

FIGS. 15d-f illustrate one method of presenting optimum predicted kinematic (i.e., motion) performance or presenting kinetic computer simulation results for different simulation iterations. While the information shown in FIGS. 15d-f is presented in the form of one or more charts, die information may be presented in other forms such as one or more tables, graphs, flowcharts, spreadsheets, data arrays, data lists, or exported data files for use with analysis software. Each chair may include information concerning one or more optimum implant placements based on kinematic analysis or one or more expected performance characteristics, values, or results corresponding to said one or more optimum implant placements. Alternatively, the charts may simply show the expected kinematic performance for each geometric configuration/relationship during each iteration of an iterative computer simulation. By comparing the simulation iteration results side by side, a kinematically optimum geometric configuration/relationship between implants and/or the patient's anatomy can be selected.

Figure 16:
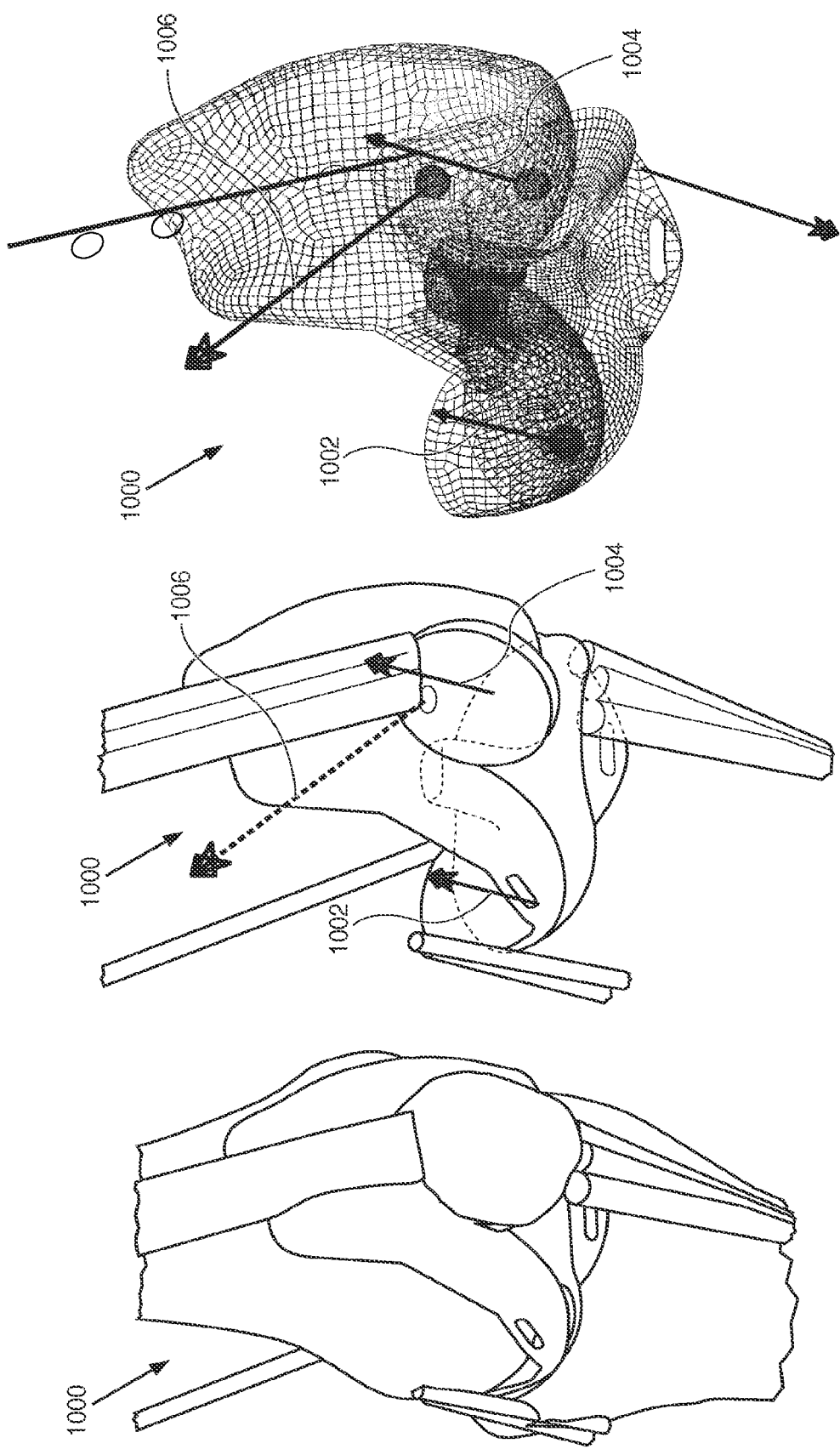
FIG. 16 illustrates a force environment snapshot during one iteration of a patient-specific computer model simulation according to some embodiments. The snapshot shows magnitudes and directions of prosthesis and soft tissue forces for a particular prosthesis configuration relative to a particular patient's anatomy.

FIG. 16 illustrates a computer simulation model (1000) according to some embodiments. The model (1000) may be, for Instance, part of a submodel (920). During each iteration, the model (1000) records magnitudes and directions of forces (1002, 1004, 1006) in order to characterize an iteration force environment. Iteration force environments can be uploaded to a database that applies user-defined thresholds set by a surgeon or engineer. The user-defined thresholds may include minimum acceptable requirements for at least one performance characteristic. Performance characteristics may relate to, without limitation, wear ($mm^3$ per million cycles), stress, range of motion (ROM), kinematics (e.g., tibiofemoral and patellofemoral interactions, anterior-posterior translation, flexion, internal/external tibial or femoral rotation, patella flexion, patella tilt, patella spin, femoral rollback), kinetics (e.g., compressive forces, forces contributing to shear, torque, anterior-posterior forces, medial-lateral forces, and flexion moments acting on implant components), biomechanics, implant robustness, fatigue life, fixation strength, shear loading at cement or ingrowth interface, bony impingement, soft-tissue impingement, joint laxity, subluxation, subsidence, ligament balancing, ligament force, quadriceps force, knee efficiency, patellar femoral impingement, Q-angle, stability, anatomic bone fit, implant longevity, and natural postoperative feeling (no pain and good proprioception).

EXAMPLES

In a first example of the present invention, a candidate for knee surgery who enjoys running will be measured while performing several various activities with an emphasis on uphill, downhill, and level jogging. The candidate's functional characterization may be determined by performing said activities on a treadmill or inclined force plate while jogging in place. It may be determined through steps (110), (112), and (114) that said candidate generally tends to have-more external rotation in full extension than is normal (i.e., the patient has an out-toeing abnormality). In this instance, iterative model simulation may be used to characterize and analyze the patient's jog on the computer with a virtually-implanted Smith & Nephew Legion™ Primary system. The simulation results might indicate that the tibial component should be positioned with slightly greater posterior slope than normal, so as to give the patient more postoperative AP stability (tibial drawer test), since this orientation may prevent anterior femoral slide off, reduce the possibility of PCL damage/pain, and decrease anterior wear by placing the bearing surface more orthogonal to the mechanical force line during heel-strike.

In a second example of the present invention, a person with an abnormally high quadriceps angle (Q-angle) is arthritic in the medial condyle and has an ACL deficiency. The person enjoys hiking in the mountains and gardening. The biomechanic function of the patient is measured and quantified during several activities with a focus on stair climb, squatting sequences and kneeling sequences. Information obtained during the patient's participation in said activities is imported into three universal computer models to create three patient-specific computer models for each of stair climb, squatting, and kneeling. To facilitate analysis, the models may be spliced to create a single progression model (in other words, a single patient-specific model is created which includes a progression of stair climb sequence, squat sequence and then kneel sequence). A Journey™ Bi-cruciate stabilized (BCS) knee system model is virtually installed in the patient by importing a 3D CAD model of the Journey™ BCS system into the patient-specific computer models. Each model may be run through hundreds of iterations, wherein the variables pertaining orientation and/or size of the implant components are slightly adjusted during each iteration. After the computer models finish their iterations, a program generally Indicates one or more suggested surgical plans, including optimal positions and sizes of the implant components relative to the patient's anatomy and other implant components. The suggested orientations take into consideration the patient's abnormal patella tracking pattern so as to reduce post-operative anterior knee pain, and also positions the implant components to obtain the best possible stability between 10 and −10 degrees of flexion (i.e., an angle which sees high patellar shear forces during hiking). Anatomic fit performance (802) is considered simultaneously throughout computer model simulation. Digital information from the model is then exported to a rapid manufacturing machine which produces custom cutting blocks configured to guide resections and holes which will reproduce the same implant position as the optimum position determined by the computer model. If custom cutting blocks are not preferred over standard instrumentation, a CAS system may use the digital information exported from the simulation to guide resections and holes such that the implant will be positioned in the same manner as the optimum position determined by the computer model. Moreover, if CAS and custom blocks are not desirable, the digital information may be used to configure an adjustable standard cutting jug to facilitate optimum implantation.

Although the invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

For example, computerized tomography (CT), magnetic resonance imaging (MRI), ultrasound, Digital X-ray, and other forms of anatomic radiological imaging may be advantageously be utilized with the present invention to form patient-specific instrumentation that guides the path of a surgical cutting tool according to the best computer model results. In other words, patient-specific knee cutting blocks may be created from an individual patient's biomechanic characterization, said blocks comprising any of holes, slots, oscillating saw blade guides, and mill guides oriented so that the final prosthesis component orientations will match the optimal prosthesis component orientations indicated by the computer model.

In another example, the computer modeling simulations may be performed after optimum implant component orientation(s) have already been determined, in cider to assess and predict long term wear performance characteristics. That is, one or more virtually-implanted implant components can be run through a specified number of simulation cycles (e.g., 2 million), in order to determine: 1) what the expected wear performance characteristics will be in a specified number of years (e.g., twenty years), and 2) how that wear will affect other biomechanic performance factors and anatomic fit over time (i.e., worsening bone coverage due to stress shielding and subsidence). Of course such long-term wear modeling may require more detailed input concerning implant material properties.

In yet even another example, a surgeon may wish to tune specific performance characteristics. For example, for young and active patients, a surgeon may wish to place more importance on fixation strength than other performance characteristics.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

The following is claimed:

1. A process for selecting prosthetic implant parameters optimized to a particular patient's biomechanical characterization, comprising:
    obtaining, from at least one of a CT device, an MRI device, a radiological device, an ultrasound device and an X-ray device, image data of a patient joint;
    deriving, using a computing device, from the image data, a plurality of dimensions including at least one dimension that includes at least one of anatomic landmark data and soft tissue attachment data of the patient joint;
    executing, using the computer device, a plurality of simulations of a joint model approximating the patient joint, based on the plurality of dimensions, having one or more a prosthetic implant components with size and position variables relative to the plurality of dimensions, wherein the joint model undergoes a motion profile associated with a selected patient activity and at least one of the size and position variables differs with each simulation; and
    calculating, from the plurality of simulations, and outputting by the computing device a recommendation of at least one of implant size, implant position, and ligamentous releases.

2. The process of claim 1, wherein the step of obtaining image data of the patient comprises performing an anatomical scan of the patient.

3. The process of claim 2, further comprising the step of extracting the anatomic landmark data from the anatomical scan to create a bone model of the patient or a patient population.

4. The process of claim 3, further comprising the step of re-orienting or scaling the bone model by at least one dimension.

5. The process of claim 4, wherein the step of re-orienting or scaling the bone model by at least one dimension comprises aligning the bone model with a standard reference frame and scale.

6. The process of claim 3, further comprising importing the bone model into a CAD software package.

7. The process of claim 3, further comprising the step of subjecting the bone model to a segmentation filter.

8. The process of claim 1, further comprising the step of determining the mechanical axis.

9. The process of claim 1, wherein the method further includes the step of determining at least one cutting plane for a patient's bone.

10. A method for selecting prosthetic implant parameters optimized for a particular patient, the method comprising:

receiving, from at least one of a CT device, an MRI device, a radiological device, an ultrasound device and an X-ray device, image data of a patient joint;

deriving, using a computing device, from the image data, a plurality of dimensions including at least one dimension that includes at least one of bone morphology data and soft tissue attachment data of the patient joint;

executing, using the computer device, a plurality of simulations of a joint model approximating the patient joint, based on plurality of dimensions having one or more a prosthetic implant components with size and position variables relative to the plurality of dimensions, wherein the joint model undergoes a motion profile associated with a selected patient activity and at least one of the size and position variables differs with each simulation; and calculating, from the plurality of simulations, and outputting by the computing device a recommendation of at least one of implant size, implant position, and ligamentous releases.

11. The method of claim 10, wherein the step of receiving image data of the patient comprises performing an anatomical scan of the patient.

12. The method of claim 11, further comprising the step of extracting anatomic landmark data from the anatomical scan to create a bone model of the patient or a patient population.

13. The method of claim 12, further comprising the step of re-orienting or scaling the bone model by at least one dimension.

14. The method of claim 13, wherein the step of re-orienting or scaling the bone model by at least one dimension comprises aligning the bone model with u standard reference frame and scale.

15. The method of claim 12, further comprising importing the bone model into a CAD software package.

16. The method of claim 12, further comprising the step of subjecting the bone model to a segmentation filter.

17. The method of claim 10, further comprising the step of determining the mechanical axis.

18. The method of claim 10, wherein the method further includes the step of determining cutting planes for a patient's bone.

* * * * *